(12) United States Patent
Zhao et al.

(10) Patent No.: US 7,928,095 B2
(45) Date of Patent: *Apr. 19, 2011

(54) TREATMENT OF RESISTANT OR REFRACTORY CANCERS WITH MULTI-ARM POLYMERIC CONJUGATES OF 7-ETHYL-10-HYDROXYCAMPTOTHECIN

(75) Inventors: Hong Zhao, Edison, NJ (US); Puja Sapra, Edison, NJ (US)

(73) Assignee: Enzon Pharmaceuticals, Inc., Bridgewater, NJ (US)

( * ) Notice: Subject to any disclaimer, the term of this patent is extended or adjusted under 35 U.S.C. 154(b) by 223 days.

This patent is subject to a terminal disclaimer.

(21) Appl. No.: 12/028,378

(22) Filed: Feb. 8, 2008

(65) Prior Publication Data

US 2008/0193408 A1 Aug. 14, 2008

Related U.S. Application Data

(60) Provisional application No. 60/900,592, filed on Feb. 9, 2007.

(51) Int. Cl.
| | |
|---|---|
| *A61K 31/33* | (2006.01) |
| *A61K 31/194* | (2006.01) |
| *A61K 31/235* | (2006.01) |
| *A61K 31/426* | (2006.01) |
| *A61P 3/10* | (2006.01) |

(52) U.S. Cl. .................................................. 514/183
(58) Field of Classification Search .................. 514/183
See application file for complete search history.

(56) References Cited

U.S. PATENT DOCUMENTS

| | | | |
|---|---|---|---|
| 4,473,692 | A | 9/1984 | Miyasaka et al. |
| 4,943,579 | A | 7/1990 | Vishnuvajjala et al. |
| 5,614,549 | A | 3/1997 | Greenwald et al. |
| 5,648,506 | A | 7/1997 | Desai et al. |
| 5,681,567 | A | 10/1997 | Martinez et al. |
| 5,736,156 | A * | 4/1998 | Burke ........................ 424/450 |
| 5,840,900 | A | 11/1998 | Greenwald et al. |
| 5,840,973 | A | 11/1998 | Yasukohchi et al. |
| 5,859,022 | A | 1/1999 | Hausheer et al. |
| 5,880,131 | A | 3/1999 | Greenwald et al. |
| 5,902,588 | A | 5/1999 | Greenwald et al. |
| 5,948,155 | A | 9/1999 | Yui et al. |
| 5,965,566 | A | 10/1999 | Greenwald et al. |
| 6,011,042 | A | 1/2000 | Greenwald et al. |
| 6,111,107 | A | 8/2000 | Greenwald et al. |
| 6,121,451 | A | 9/2000 | Henegar et al. |
| 6,127,355 | A | 10/2000 | Greenwald et al. |
| 6,153,655 | A | 11/2000 | Martinez et al. |
| 6,177,087 | B1 | 1/2001 | Greenwald et al. |
| 6,194,580 | B1 | 2/2001 | Greenwald et al. |
| 6,281,223 | B1 | 8/2001 | Henry |
| 6,395,266 | B1 | 5/2002 | Martinez et al. |
| 6,403,569 | B1 | 6/2002 | Achterrath |
| 6,534,293 | B1 | 3/2003 | Barany et al. |
| 6,608,076 | B1 | 8/2003 | Greenwald et al. |
| 6,638,499 | B2 | 10/2003 | Martinez et al. |
| 6,649,778 | B1 | 11/2003 | Zhao et al. |
| 6,723,338 | B1 * | 4/2004 | Sarris et al. .................... 424/450 |
| 6,756,037 | B2 | 6/2004 | Greenwald et al. |
| 6,875,841 | B2 | 4/2005 | Sakanoue et al. |
| 6,897,200 | B1 * | 5/2005 | Burke et al. .................... 514/44 |
| 2001/0041172 | A1 | 11/2001 | Bentley et al. |
| 2002/0002250 | A1 | 1/2002 | Bentley et al. |
| 2002/0016285 | A1 | 2/2002 | Bhatt et al. |
| 2002/0077279 | A1 | 6/2002 | Kumar et al. |
| 2002/0182172 | A1 | 12/2002 | Bentley et al. |
| 2003/0105275 | A1 | 6/2003 | Bentley et al. |
| 2004/0009229 | A1 | 1/2004 | Unger et al. |
| 2004/0058981 | A1 | 3/2004 | Lai et al. |
| 2004/0077595 | A1 | 4/2004 | Cheng et al. |
| 2004/0156858 | A1 | 8/2004 | Franzusoff et al. |
| 2004/0247624 | A1 | 12/2004 | Unger et al. |
| 2005/0112088 | A1 | 5/2005 | Zhao et al. |
| 2005/0214250 | A1 | 9/2005 | Harris et al. |
| 2005/0226843 | A1 | 10/2005 | Bentley et al. |
| 2006/0135527 | A1 * | 6/2006 | Houghton et al. ........ 514/252.18 |
| 2007/0173615 | A1 | 7/2007 | Zhao et al. |
| 2007/0259375 | A1 | 11/2007 | Ford et al. |

| | | | |
|---|---|---|---|
| 2008/0058364 | A1 | 3/2008 | Sapra |
| 2008/0193408 | A1 | 8/2008 | Zhao et al. |
| 2009/0074704 | A1 | 3/2009 | Zhao et al. |

FOREIGN PATENT DOCUMENTS

| | | |
|---|---|---|
| EP | 0757049 B1 | 3/1999 |
| WO | 9841562 | 9/1998 |
| WO | 0064486 | 11/2000 |
| WO | 0168066 A3 | 9/2001 |
| WO | 0174402 | 10/2001 |
| WO | 02089789 A1 | 11/2002 |
| WO | 03031467 | 4/2003 |
| WO | 03037384 | 5/2003 |
| WO | 03037385 A1 | 5/2003 |
| WO | 2004060967 | 7/2004 |
| WO | 2007092646 A2 | 8/2007 |

OTHER PUBLICATIONS

Cecil Textbook of Medicine, edited by Lee Goldman and J. Claude Bennett, 21st Edition, vol. 1, Chapter 14, pp. 1060-1074 (2000).*
Carpino, L. A., et al., New family of base- and nucleophile-sensitive amino-protecting groups. A Michael-acceptor-based deblocking process. Practical utilization of the 1,1-dioxobenzo[b]thiophene-2-ylmethylcarbonyl (Bsmoc) group, Journal of the American Chemical Society, 119: 9915-9916, 1997.
Chabot, G. G., Clinical pharmacokinetics or irinotecan, Clinical Pharmacokinet, 33: 245-259, 1997.
Choe, Y. H., et al., Anticancer drug delivery systems: N4-acyl-poly(ethyleneglycol) prodrugs of ara-C. I. Efficacy in solid tumors, Journal of Controlled Release, 79: 41-53, 2002.
Conover, C. D., et al., Campothecin delivery systems: enhanced efficacy and tumor accumulation of campotothecin following its conjugation to polyethylene glycol via a glycine linker, Cancer Chemotherapy Pharmacology, 407-414, 1998.
Duncan, R., Polymer conjugates as anticancer nanomedicines, Nature Reviews: Cancer, 6: 688-701, 2006.
Garcia-Carbonero, R., et al., Current perspectives on the clinical experience, pharmacology, and continued development of the camptothecins, Clinical Cancer Research, 8:641-661, 2002.
Gottlieb, J. A., et al., Preliminary pharmacologic and clinical evaluation of camptothecin sodium (NSC-100880), Cancer Chemotherapy Reports, 54: 461-470, 1970.
Greenwald, R. B., et al., Synthesis, isolation, and characterization of 2'-paclitaxel glycinate: an application of the Bsmoc protecting group, Journal of Organic Chemistry, 68: 4894-6, 2003.
Greenwald, R. B., et al., Drug delivery systems. 2. Camptothecin 20-O-poly(ethylene glycol) ester transport forms, Journal of Medicinal Chemistr, 39: 1938-1940, 1996.
Greenwald, R. B., et al., Drug delivery systems: water soluble taxol 2'-poly(ethylene glycol) ester prodrugs-Design and in vivo effectiveness, Journal of Medicinal Chemistry, 39: 424-431, 1996.
Greenwald, R. B., et al., Effective drug delivery by PEGylated drug conjugates, Advanced Drug Delivery Reviews, 55: 217-250, 2003.
Kaneda, N., et al., Metabolism and pharmacokinetics of the camptothecin analogue CPT-11 in the mouse, Cancer Research, 50:1715-1720, 1990.
Kawato, Y., et al., Intracellular roles of SN-38, a metabolite of the camptothecin derivative CPT-11, in the antitumor effect of CPT-11, Cancer Research, 51: 4187-4191, 1991.
Liu, X., et al., Degradation of camptothecin-20(S)-glycinate ester prodrug under physiological conditions, Journal of Pharmaceutical and Biomedical Analysis, 35: 1113-1125, 2004.
Maeda, H., et al., Tumor vascular permeability and the EPR effect in macromolecular therapeutics: a review, Journal of Controlled Release, 65: 271-284, 2000.
Mathijssen, R. H. J., et al., Clinical pharmacokinetics and metabolism of irinotecan (CPT-11), Clinical Cancer Research, 7: 2182-2194, 2001.
NOF Corp. Drug Delivery System catalog, ver. 8.
Pommier, Y., Topoisomerase I inhibitors: camptothecins and beyond, Nature Reviews: Cancer, 6: 789-802, 2006.
Rowinsky, E. K., et al., A Phase I and pharmacokinetic study of pegylated camptothecin as a 1-hour infusion every 3 weeks in patients with advanced solid malignancies, Journal of Clinical Oncology, 148-157, 2003.
Senter, P. D., et al., Identification and activities of human carboxylesterases for the activation of CPT-11, a clinically approved anticancer drug, Bioconjugate Chemistry, 12: 1074-1080, 2001.
Slatter, J. G., et al., Bioactivation of the anticancer agent CPT-11 to SN 38 by human hepatic microsomal carboxylesterases and the in vitro assessment of potential drug interactions, Drug Metabolism and Disposition, 25: 1157-1164, 1997.
Slatter, J. G., et al., Pharmacokinetics, metabolism, and excretion of irinotecan (CPT-11) following i.v. infusion of [14C]CPT-11 in cancer patients, Drug Metabolism and Disposition, 28: 423-433, 2000.
Smith, N. F., et al., Pharmacogenetics of irinotecan metabolism and transport: an update, Toxicology in Vitro, 20: 163-175, 2006.
Ulukan, H., et al., Camptothecins: a review of their chemotherapeutic potential, Drugs, 62: 2039-57, 2002.
Zhang, J. A., et al., Development and characterization of a novel liposome-based formulation of SN-38, International Journal of Pharmaceutics, 270: 93-107, 2004.
Zhao, H., et al., 20-O-acylcamptothecin derivatives: evidence for lactone stabilization, Journal of Organic Chemistry, 65: 4601-4606, 2000.
Greenwald, R. B., et al., Camptothecin-20-PEG ester transport forms: the effect of spacer groups on antitumor activity, Bioorganic & Medicinal Chemistry, 6: 551-562, 1998.
Conover, C. D., et al., Camptothecin delivery systems: the utility of amino acid spacers for the conjugation of camptothecin with polyethylene glycol to create prodrugs, Anticancer Drug Design, 14: 499-506, 1999.
Zalipsky et al., Attachments Of Drugs To Polyethylene Glycols, European Polymer Journal, 1983, 19(12): 1177-1183.
Greenwald et al., Poly(ethylene glycol) Conjugated Drugs and Prodrugs: A Comprehensive Review, Critical Review in Therapeutic Drug Carrier Systems, 2000, 17(2): 101-161.
Office Action issued in U.S. Appl. No. 11/840,773 and dated May 7, 2009.
Office Action issued in U.S. Appl. No. 12/274,474 and dated May 8, 2009.
International Search Report and Written Opinion issued in PCT/US08/53438 and dated Oct. 17, 2008.
International Search Report and Written Opinion dated Aug. 13, 2008 and issued in PCT/US2007/03808.
International Search Report and Written Opinion issued in PCT/US07/76241 and dated Aug. 8, 2008.
International Search Report and Written Opinion issed in PCT/US09/55319 and dated Dec. 31, 2009.
Nemunaitis et al., Irinotecan Hydrochloride (CPT-11) Resistance Identified by K-ras Mutation in Patients with Progressive Colon Cancer After Treatment with 5-fluorouracil (5-FU), American Journal of Clinical Oncology, Oct. 1997, 20(5): 527-529.
Allen et al., Role of Genomic Markers in Colorectal Cancer Treatment, JJClin Oncol Apr. 12, 2005, 23(20): 4545-4552.
Padilla de Jesus et al., Polyester Dendritic Systems for Drug Delivery Applications: In Vitro and In Vivo Evaluation, Bioconjugate Chem. 13:453-461, 2002.
Warnecke et al., Maleimide-oligo(ethylene glycol) derivatives of Camptothecin as Albumin-binding Prodrugs: Synthesis and Antitumor Efficacy, Bioconjugate Chem. 14:377-387, 2003.

* cited by examiner

*Primary Examiner* — Ardin Marschel
*Assistant Examiner* — Alicia R Hughes
(74) *Attorney, Agent, or Firm* — Lucas & Mercanti, LLP

(57) ABSTRACT
A method of treating a resistant or refractory cancer in a mammal includes administering an effective amount of a compound of
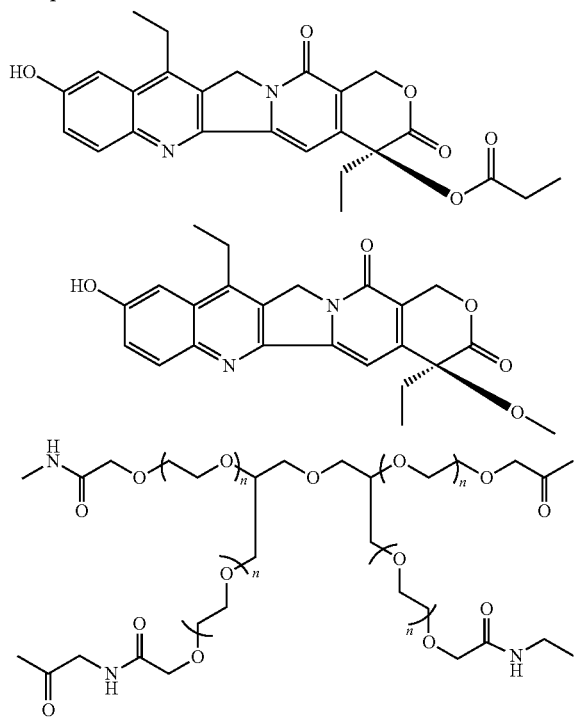
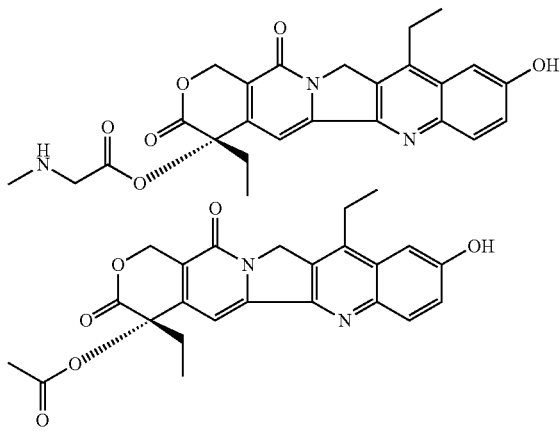
to the mammal. In preferred aspects, the cancer is resistant or refractory to CPT-11 or CPT therapy.
29 Claims, 4 Drawing Sheets

TREATMENT OF RESISTANT OR REFRACTORY CANCERS WITH MULTI-ARM POLYMERIC CONJUGATES OF 7-ETHYL-10-HYDROXYCAMPTOTHECIN

CROSS-REFERENCE TO RELATED APPLICATION

This application claims the benefit of priority from U.S. Provisional Patent Application Ser. No. 60/900,592 filed Feb. 9, 2007, the contents of which are incorporated herein by reference.

FIELD OF INVENTION

The present invention relates to a method of treating resistant or refractory cancers. In particular, the invention relates to a method of treating cancers resistant or refractory to camptothecin or CPT-11 using polyethylene glycol conjugates of 7-ethyl-10-hydroxycamptothecin.

BACKGROUND OF INVENTION

Over the years, there have been reports that many common cancers have shown resistance or refractory phenomenon to curative therapies. Some cancers do not respond or respond initially but shortly thereafter, they become resistant to the therapies. Other cancers fail to respond to therapies which include subsequent rounds of treatment after earlier successful rounds of treatment. In other cases, cancers recur several years after completing effective treatment. If the resistance or refractory phenomenon to chemotherapy, radiation therapy or other cancer therapies could be prevented or overcome, it would be a great advance in medicine.

Various anti-cancer agents have been developed in efforts to treat cancers. Many of those potential anti-cancer agents have unfortunately shown drug resistance through a variety of mechanisms. Some tumors do not respond to certain types of anti-cancer agents after initial short therapeutic responses are shown. In some cases, tumor shrinkage reverses and tumors start to grow again in spite of the cancer initially responding to anti-cancer agents.

One potent anti-cancer agent is camptothecin. Camptothecin and related analogs are known as DNA topoisomerase I inhibitors. Irinotecan (CPT-11, Camptosar®) is a currently marketed DNA topoisomerase I inhibitor with some anticancer activity. Although not currently marketed, an active metabolite of CPT-11, 7-ethyl-10-hydroxycamptothecin, is thought to also have some anticancer activity. Like other anticancer agents, drug resistance has been observed with the use of camptothecin and camptothecin derivatives. For example, resistance to 9-amino or 9-nitro substituted camptothecins has been reported in common cancers. See U.S. Pat. No. 6,194,579.

Various proposals have been made to overcome drug resistance or refractory phenomenon associated with anti-cancer agents. One early attempt to overcome the barrier associated with camptothecin or camptothecin analogs was directed to developing less toxic CPT derivatives. Other attempts include uses of potential drug resistance blockers such as an epidermal growth factor receptor antagonist and $Na^+/K^+$ ATPase inhibitors. See US Patent Publication Nos. 2002/0012663 and 2006/0135468.

In spite of the attempts and advances, there continues to be a need to provide a method of treating a resistant or refractory cancer. The present invention addresses this need.

SUMMARY OF INVENTION

In order to overcome the above problems and improve the therapy for treatment of cancers, there is provided a method of treating a resistant or refractory cancer in a mammal.

In one aspect of the invention, there is provided a method of treating a resistant or refractory cancer in a mammal, including:

administering an effective amount of a compound of formula (I):

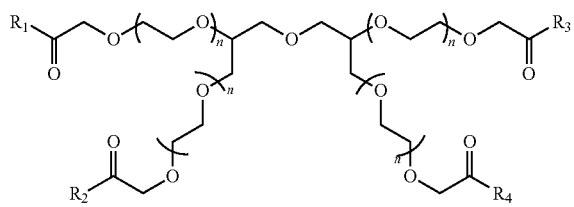

(I)

wherein $R_1$, $R_2$, $R_3$ and $R_4$ are independently OH or

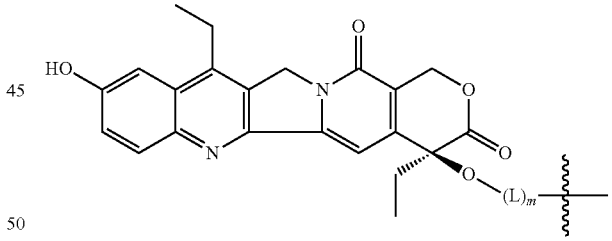

wherein

L is a bifunctional linker;

m is 0 or a positive integer; and n is a positive integer;

provided that $R_1$, $R_2$, $R_3$ and $R_4$ are not all OH;

or a pharmaceutically acceptable salt thereof to the mammal.

In one particular aspect of the invention, the polymeric prodrugs of 7-ethyl-10-hydroxycamptothecin for treatment of the resistant or refractory cancer employ four-arm PEG-7-ethyl-10-hydroxycamptothecin conjugates having the structure of

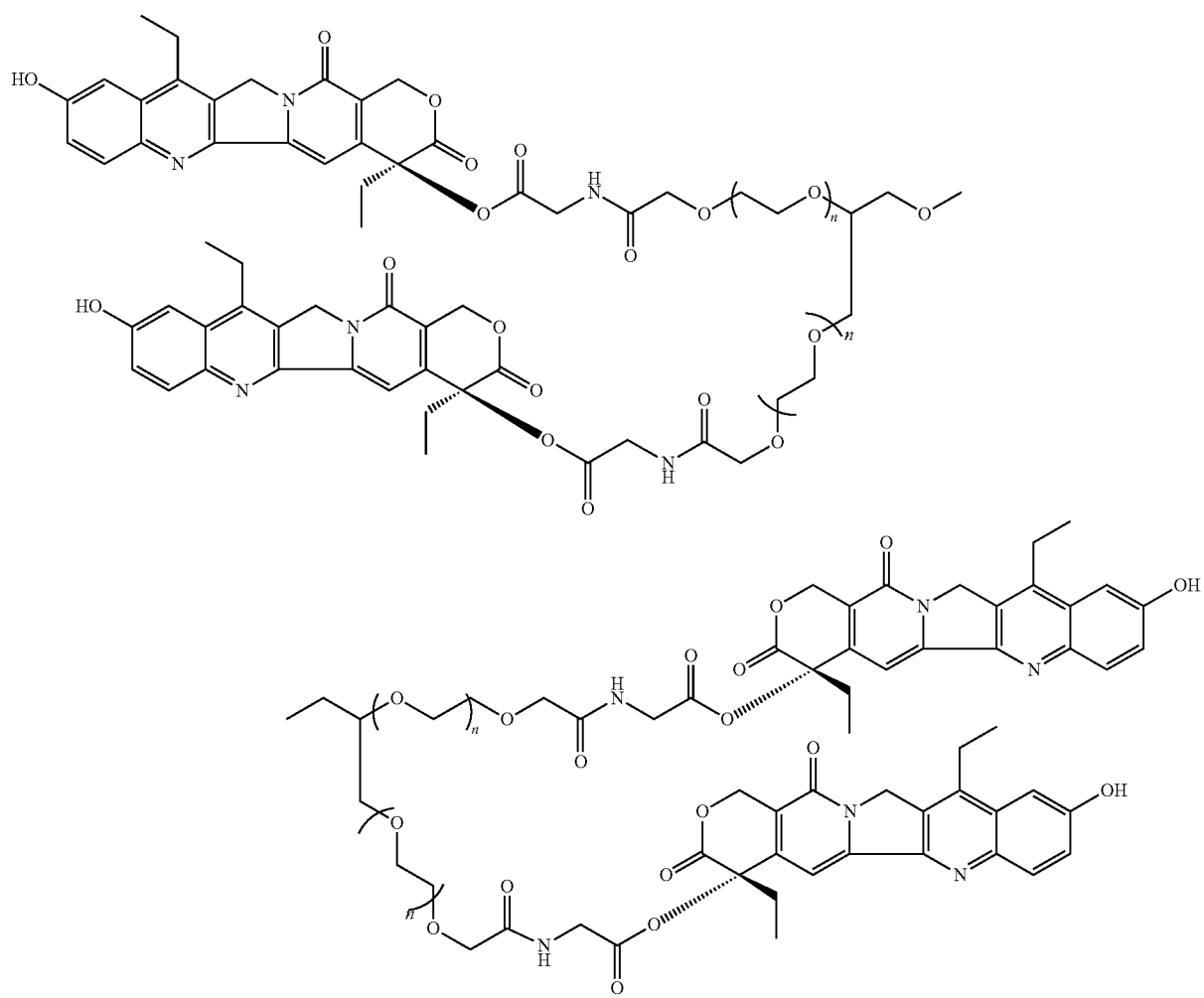

wherein n is from about 28 to about 341, preferably from about 114 to about 227, and more preferably about 227.

The resistant or refractory cancers which can be treated with the methods described herein include solid tumors, lymphomas, lung cancer, small cell lung cancer, acute lymphocytic leukemia (ALL), breast cancer, colorectal cancer, pancreatic cancer, glioblastoma, ovarian cancer and gastric cancer. The forgoing list is not meant to be exclusive and those of ordinary skill will, of course, realize that other resistant or refractory cancers not specifically mentioned herein are intended for inclusion.

One aspect of the invention provides the method of treating cancers resistant or refractory to chemotherapy. In one particular aspect, the treatment is effective for cancers resistant or refractory to camptothecin (CPT) or CPT-11. associated therapy. Alternatively, the present invention provides a method of treating cancers showing topoisomerase I mediated resistance or refractory phenomenon.

In another aspect, the present invention provides a method of treating cancers resistant or refractory to therapies associated with administration of polymeric prodrug forms of CPT or CPT-11 such as polyethylene glycol conjugates of CPT or CPT-11.

The polymeric prodrugs of 7-ethyl-10-hydroxycamptothecin according to the present invention are effective to cancers resistant or refractory at the onset of treatment or subsequent round therapies. The present invention allows treatment of refractory cancers that are sensitive to CPT-11, i.e. which appear to be inhibited in the first round treatment but become resistant to in the second or subsequent rounds of therapies. The polymeric prodrugs of 7-ethyl-10-hydroxycamptothecin can be further effective for treatment of recurring cancers after treatment is discontinued.

In another aspect of the invention, the polymeric prodrugs of 7-ethyl-10-hydroxy-camptothecin are administered in amounts of from about 0.1 to about 45 mg/m$^2$/dose based on the non-polymer portion of the conjugate. The polymeric prodrugs described herein are administered once every three weeks for each treatment cycle or once weekly for three weeks, followed by one week rest period for each cycle until the desired results are observed.

One advantage of the present invention is that patients can be treated concurrently or sequentially with an effective amount of the polymeric prodrugs of 7-ethyl-10-hydroxy-camptothecin in combination with another anti-cancer therapeutic agent for synergistic benefit.

Yet another advantage of the present invention is that the prodrug formulations described herein have reduced the toxicity and/or overcome difficulties encountered when compared to prior art pharmaceutical preparations.

Other and further advantages will be apparent from the following description and drawings.

For purposes of the present invention, the term "residue" shall be understood to mean that portion of a compound, to which it refers, i.e. 7-ethyl-10-hydroxycamptothecin, amino acid, etc. that remains after it has undergone a substitution reaction with another compound.

For purposes of the present invention, the term "polymeric containing residue" or "PEG residue" shall each be understood to mean that portion of the polymer or PEG which remains after it has undergone a reaction with 7-ethyl-10-hydroxycamptothecin-containing compounds.

For purposes of the present invention, the term "alkyl" as used herein refers to a saturated aliphatic hydrocarbon, including straight-chain, branched-chain, and cyclic alkyl groups. The term "alkyl" also includes alkyl-thio-alkyl, alkoxyalkyl, cycloalkylalkyl, heterocycloalkyl, $C_{1-6}$ hydrocarbonyl, groups. Preferably, the alkyl group has 1 to 12 carbons. More preferably, it is a lower alkyl of from about 1 to 7 carbons, yet more preferably about 1 to 4 carbons. The alkyl group can be substituted or unsubstituted. When substituted, the substituted group(s) preferably include halo, oxy, azido, nitro, cyano, alkyl, alkoxy, alkyl-thio, alkyl-thio-alkyl, alkoxyalkyl, alkylamino, trihalomethyl, hydroxyl, mercapto, hydroxy, cyano, alkylsilyl, cycloalkyl, cycloalkylalkyl, heterocycloalkyl, heteroaryl, alkenyl, alkynyl, $C_{1-6}$ hydrocarbonyl, aryl, and amino groups.

For purposes of the present invention, the term "substituted" as used herein refers to adding or replacing one or more atoms contained within a functional group or compound with one of the moieties from the group of halo, oxy, azido, nitro, cyano, alkyl, alkoxy, alkyl-thio, alkyl-thio-alkyl, alkoxyalkyl, alkylamino, trihalomethyl, hydroxyl, mercapto, hydroxy, cyano, alkylsilyl, cycloalkyl, cycloalkylalkyl, heterocycloalkyl, heteroaryl, alkenyl, alkynyl, $C_{1-6}$ hydrocarbonyl, aryl, and amino groups.

The term "alkenyl" as used herein refers to groups containing at least one carbon-carbon double bond, including straight-chain, branched-chain, and cyclic groups. Preferably, the alkenyl group has about 2 to 12 carbons. More preferably, it is a lower alkenyl of from about 2 to 7 carbons, yet more preferably about 2 to 4 carbons. The alkenyl group can be substituted or unsubstituted. When substituted the substituted group(s) preferably include halo, oxy, azido, nitro, cyano, alkyl, alkoxy, alkyl-thio, alkyl-thio-alkyl, alkoxyalkyl, alkylamino, trihalomethyl, hydroxyl, mercapto, hydroxy, cyano, alkylsilyl, cycloalkyl, cycloalkylalkyl, heterocycloalkyl, heteroaryl, alkenyl, alkynyl, $C_{1-6}$ hydrocarbonyl, aryl, and amino groups.

The term "alkynyl" as used herein refers to groups containing at least one carbon-carbon triple bond, including straight-chain, branched-chain, and cyclic groups. Preferably, the alkynyl group has about 2 to 12 carbons. More preferably, it is a lower alkynyl of from about 2 to 7 carbons, yet more preferably about 2 to 4 carbons. The alkynyl group can be substituted or unsubstituted. When substituted the substituted group(s) preferably include halo, oxy, azido, nitro, cyano, alkyl, alkoxy, alkyl-thio, alkyl-thio-alkyl, alkoxyalkyl, alkylamino, trihalomethyl, hydroxyl, mercapto, hydroxy, cyano, alkylsilyl, cycloalkyl, cycloalkylalkyl, heterocycloalkyl, heteroaryl, alkenyl, alkynyl, $C_{1-6}$ hydrocarbonyl, aryl, and amino groups. Examples of "alkynyl" include propargyl, propyne, and 3-hexyne.

The term "aryl" as used herein refers to an aromatic hydrocarbon ring system containing at least one aromatic ring. The aromatic ring can optionally be fused or otherwise attached to other aromatic hydrocarbon rings or non-aromatic hydrocarbon rings. Examples of aryl groups include, for example, phenyl, naphthyl, 1,2,3,4-tetrahydronaphthalene and biphenyl. Preferred examples of aryl groups include phenyl and naphthyl.

The term "cycloalkyl" as used herein refers to a $C_{3-8}$ cyclic hydrocarbon. Examples of cycloalkyl include cyclopropyl, cyclobutyl, cyclopentyl, cyclohexyl, cycloheptyl and cyclooctyl.

The term "cycloalkenyl" as used herein refers to a $C_{3-8}$ cyclic hydrocarbon containing at least one carbon-carbon double bond. Examples of cycloalkenyl include cyclopentenyl, cyclopentadienyl, cyclohexenyl, 1,3-cyclohexadienyl, cycloheptenyl, cycloheptatrienyl, and cyclooctenyl.

The term "cycloalkylalkyl" as used herein refers to an alklyl group substituted with a $C_{3-8}$ cycloalkyl group. Examples of cycloalkylalkyl groups include cyclopropylmethyl and cyclopentylethyl.

The term "alkoxy" as used herein refers to an alkyl group of indicated number of carbon atoms attached to the parent molecular moiety through an oxygen bridge. Examples of alkoxy groups include, for example, methoxy, ethoxy, propoxy and isopropoxy.

An "alkylaryl" group as used herein refers to an aryl group substituted with an alkyl group.

An "aralkyl" group as used herein refers to an alkyl group substituted with an aryl group.

The term "alkoxyalkyl" group as used herein refers to an alkyl group substituted with an alkloxy group.

The term "alkyl-thio-alkyl" as used herein refers to an alkyl-S-alkyl thioether, for example methylthiomethyl or methylthioethyl.

The term "amino" as used herein refers to a nitrogen containing group as is known in the art derived from ammonia by the replacement of one or more hydrogen radicals by organic radicals. For example, the terms "acylamino" and "alkylamino" refer to specific N-substituted organic radicals with acyl and alkyl substituent groups respectively.

The term "alkylcarbonyl" as used herein refers to a carbonyl group substituted with alkyl group.

The terms "halogen" or "halo" as used herein refer to fluorine, chlorine, bromine, and iodine.

The term "heterocycloalkyl" as used herein refers to a non-aromatic ring system containing at least one heteroatom selected from nitrogen, oxygen, and sulfur. The heterocycloalkyl ring can be optionally fused to or otherwise attached to other heterocycloalkyl rings and/or non-aromatic hydrocarbon rings. Preferred heterocycloalkyl groups have from 3 to 7 members Examples of heterocycloalkyl groups include, for example, piperazine, morpholine, piperidine, tetrahydrofuran, pyrrolidine, and pyrazole. Preferred heterocycloalkyl groups include piperidinyl, piperazinyl, morpholinyl, and pyrolidinyl.

The term "heteroaryl" as used herein refers to an aromatic ring system containing at least one heteroatom selected from nitrogen, oxygen, and sulfur. The heteroaryl ring can be fused or otherwise attached to one or more heteroaryl rings, aromatic or non-aromatic hydrocarbon rings or heterocycloalkyl rings. Examples of heteroaryl groups include, for example, pyridine, furan, thiophene, 5,6,7,8-tetrahydroisoquinoline and pyrimidine. Preferred examples of heteroaryl groups include thienyl, benzothienyl, pyridyl, quinolyl, pyrazinyl, pyrimidyl, imidazolyl, benzimidazolyl, furanyl, benzofuranyl, thiazolyl, benzothiazolyl, isoxazolyl, oxadiazolyl, isothiazolyl, benzisothiazolyl, triazolyl, tetrazolyl, pyrrolyl, indolyl, pyrazolyl, and benzopyrazolyl.

The term "heteroatom" as used herein refers to nitrogen, oxygen, and sulfur.

In some embodiments, substituted alkyls include carboxyalkyls, aminoalkyls, dialkylaminos, hydroxyalkyls and mercaptoalkyls; substituted alkenyls include carboxyalkenyls, aminoalkenyls, dialkenylaminos, hydroxyalkenyls and mercaptoalkenyls; substituted alkynyls include carboxyalkynyls, aminoalkynyls, dialkynylaminos, hydroxyalkynyls and mereaptoalkynyls; substituted cycloalkyls include moieties such as 4-chlorocyclohexyl; aryls include moieties such as napthyl; substituted aryls include moieties such as 3-bromo phenyl; aralkyls include moieties such as tolyl; heteroalkyls include moieties such as ethylthiophene; substituted heteroalkyls include moieties such as 3-methoxy-thiophene; alkoxy includes moieties such as methoxy; and phenoxy includes moieties such as 3-nitrophenoxy.

For purposes of the present invention, "positive integer" shall be understood to include an integer equal to or greater than 1 and as will be understood by those of ordinary skill to be within the realm of reasonableness by the artisan of ordinary skill.

The terms "effective amounts" and "sufficient amounts" for purposes of the present invention shall mean an amount which achieves a desired effect or therapeutic effect as such effect is understood by those of ordinary skill in the art.

DETAILED DESCRIPTION OF INVENTION

A. Overview

Figure 1:
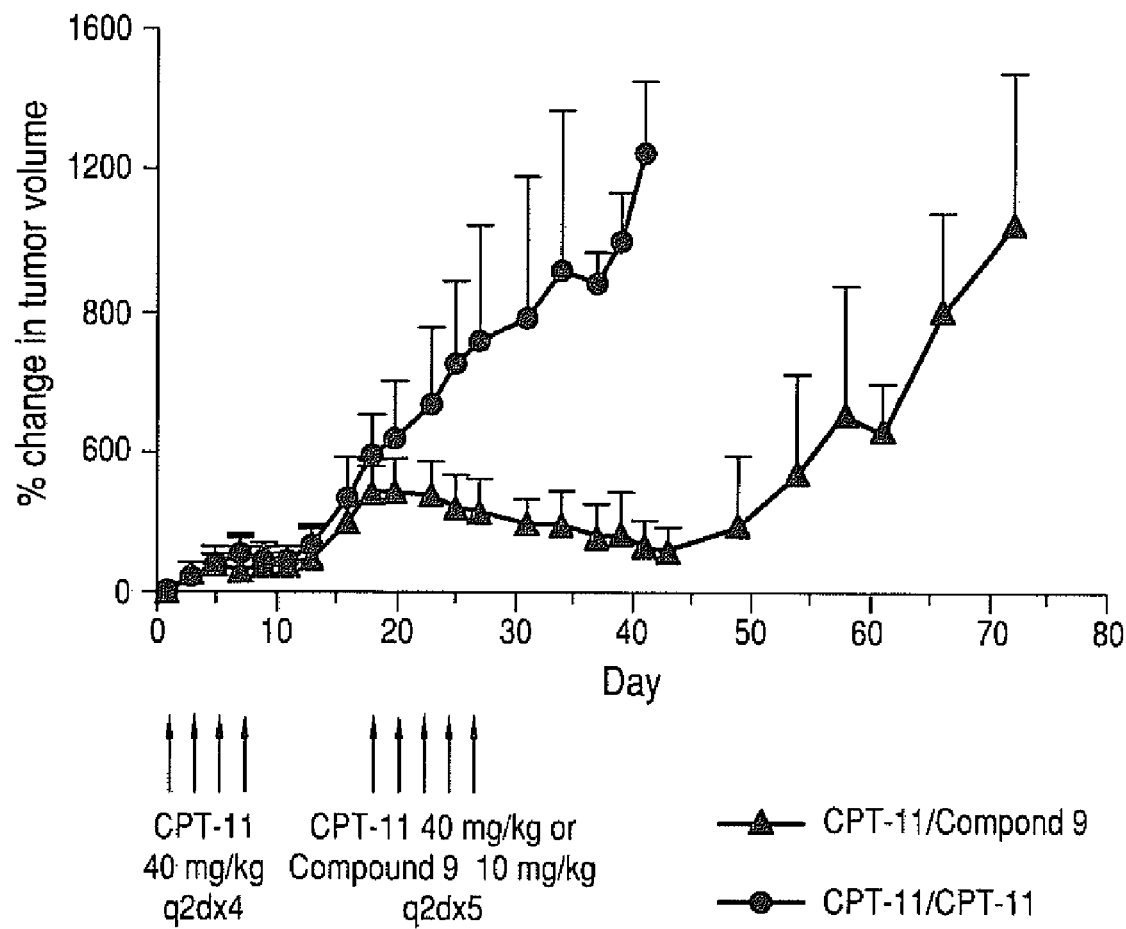
FIG. 1 shows anticancer activity of four-arm PEG-Gly-7-ethyl-10-hydroxycamptothecin in treatment of CPT-11 refractory colorectal tumor as described in Example 1.

In one aspect of the present invention, there are provided methods of treating a resistant or refractory cancer in a mammal, comprising:

administering an effective amount of a compound of formula (I):

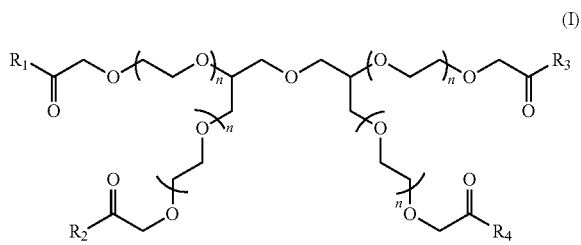

(I)

wherein
$R_1$, $R_2$, $R_3$ and $R_4$ are independently OH or

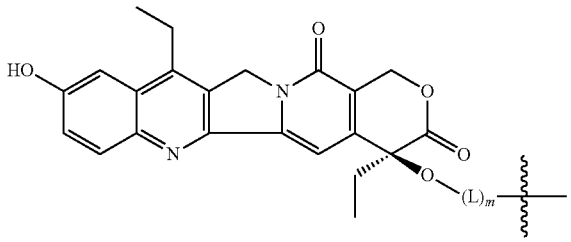

wherein
L is a bifunctional linker;
m is 0 or a positive integer, preferably 1; and
n is a positive integer;
provided that $R_1$, $R_2$, $R_3$ and $R_4$ are not all OH;
or a pharmaceutically acceptable salt thereof to the mammal in need thereof.

In an alternative embodiment, one, two or three of $R_1$, $R_2$, $R_3$ and $R_4$ can be $CH_3$.

For purposes of the present invention, refractory or resistant cancers are defined as cancers that do not respond to previous anticancer therapy or treatment. In one preferred aspect, the cancers are refractory or resistant to CPT-11 treatment. The cancers can be resistant or refractory at the beginning of treatment, or they may become resistant or refractory during treatment. Refractory cancers include tumors that do not respond at the onset of treatment or respond initially for a short period but fail to respond to treatment. Refractory cancers also include tumors that respond to treatment with anticancer therapy but fail to respond to subsequent rounds of therapies. For purposes of this invention, refractory cancers also encompass tumors that appear to be inhibited by treatment with anticancer therapy but recur up to five years, sometimes up to ten years or longer after treatment is discontinued. The anticancer therapy can employ chemotherapeutic agents alone, radiation alone or combinations thereof. For ease of description and not limitation, it will be understood that the refractory cancers are interchangeable with resistant cancers.

For purposes of the present invention, successful treatment of a resistant or refractory cancer shall be understood to mean that resistant or refractory symptoms or conditions are prevented, minimized or attenuated during and/or after anticancer treatment, when compared to that observed in the absence of the treatment described herein. The minimized, attenuated or prevented refractory conditions can be confirmed by clinical markers contemplated by the artisan in the field. In one example, successful treatment of refractory or resistant cancer shall be deemed to occur when at least 5% or preferably 10%, more preferably 20% or higher (i.e., 30, 40, 50% or more) inhibition or decrease in tumor growth and/or recurrence including other clinical markers contemplated by the artisan in the field is realized when compared to that observed in the absence of the treatment described herein. Clinical markers which show changes in the severity and magnitude of the refractory cancers can be determined by clinicians. In some aspects, the resistant or refractory cancers can be one or more of the following: solid tumors, lymphomas, small cell lung cancer, acute lymphocytic leukemia (ALL), pancreatic cancer, glioblastoma, ovarian cancer, gastric cancers, etc. The methods are useful for, among other things, treating neoplastic disease, reducing tumor burden, preventing metastasis of neoplasms and preventing recurrences of tumor/neoplastic growths in mammals. In certain aspect, the resistant or refractory cancers are solid tumors or metastatic cancers. In one particular aspect, the resistant or refractory cancer is colorectal cancer.

The present invention provides methods of treating resistant or refractory cancers to chemotherapy. In one preferred aspect, the present invention provides methods of treating cancers which are resistant or refractory to camptothecin (CPT) or camptothecin analog therapy. Alternatively, the methods described herein can be effective to treat cancers resistant or refractory to CPT or CPT analog conjugated to polymers such as polyethylene glycol. In more preferred aspect, the present invention provides methods of treating cancers which are resistant or refractory to camptothecin or CPT-11 therapy.

Camptothecin and certain related analogs share the structure:

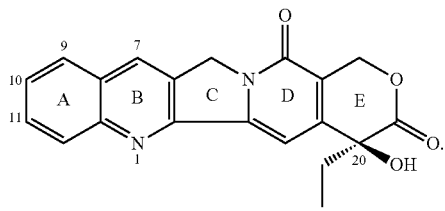

From this core structure, several known analogs have been prepared. For example, the A ring in either or both of the 10- and 11-positions can be substituted with an OH. The A ring can also be substituted with a straight or branched $C_{1-30}$ alkyl or $C_{1-17}$ alkoxy, optionally linked to the ring by a heteroatom i.e. —O or —S. The B ring can be substituted in the 7-position with a straight or branched $C_{1-30}$ alkyl (preferably $C_2$ alkyl), $C_{5-8}$ cycloakyl, $C_{1-30}$ alkoxy, phenyl alkyl, etc., alkyl carbamate, alkyl carbazides, phenyl hydrazine derivatives, etc. Other substitutions are possible in the C, D and E rings. See, for example, U.S. Pat. Nos. 5,004,758; 4,943,579; 4,473,692; RE32,518, the contents of which are incorporated herein by reference. The 10-hydroxycamptothecin, 11-hydroxycamptothecin and the 10,11-dihydroxycamtothecin analogs occur naturally as one of the minor components in *C. Acuminata* and its relatives. Additional substitutions to these compounds, i.e. 7-alkyl-, 7-substituted alkyl-, 7-amino-, 7-aminoalkyl-, 7-aralkyl-, 9-alkyl-, 9-aralkyl-camptothecin etc. derviatives are made using known synthetic techniques. Some camptotheca alkaloids have the structure shown below:

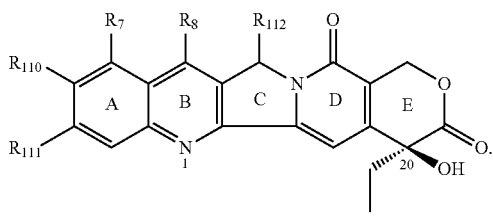

(II)

In the structure shown above $R_7$ is one of $NO_2$, $NH_2$, $N_3$, hydrogen, halogen (F, Cl, Br, I), COOH, OH, O—$C_{1-8}$ alkyl, SH, S—$C_{1-3}$ alkyl, CN, $CH_2NH_2$, NH—$C_{1-3}$ alkyl, $CH_2$—NH—$C_{1-3}$ alkyl, N($C_{1-3}$ alkyl)$_2$, $CH_2N(C_{1-3}$ alkyl), O—, NH— and S—$CH_2CH_2N(CH_2CH_2OH)_2$, O—, NH— and S—$CH_2CH_2CH_2N(CH_2CH_2OH)_2$, O—, NH— and S—$CH_2CH_2CH_2N(CH_2CH_2CH_2OH_2)_2$, O—, NH— and S—$CH_2CH_2N(C_{1-3}$ alkyl)$_2$, O—, NH— and S—$CH_2CH_2CH_2N(C_{1-3}$ alkyl)$_2$, CHO or $C_{1-3}$ alkyl.

$R_8$ in the structure (II) shown above can be H or $C_{1-8}$ alkyl (preferably $C_2$ alkyl) or $CH_2NR_9R_{10}$ where
(a) $R_9$ and $R_{10}$ are, independently, hydrogen, $C_{1-6}$ alkyl, $C_{3-7}$ cycloalkyl, $C_{3-7}$ cycloalkyl-$C_{1-6}$ alkyl, $C_{2-6}$ alkenyl, hydroxy-$C_{1-6}$ alkyl, $C_{1-6}$ alkoxy-$C_{1-6}$ alkyl; alternatively
(b) $R_9$ can be hydrogen, $C_{1-6}$ alkyl, $C_{3-7}$ cycloalkyl, $C_{3-7}$ cycloalkyl-$C_{1-6}$ alkyl, $C_{2-6}$ alkenyl, hydroxy-$C_{1-6}$ alkyl, $C_{1-6}$ alkoxy-$C_{1-6}$ alkyl and $R_{10}$ can be —$COR_{11}$ where $R_{11}$ is hydrogen, $C_{1-6}$ alkyl, perhalo-$C_{1-6}$ alkyl, $C_{3-7}$ cycloalkyl, $C_{3-7}$ cycloalkyl-$C_{1-6}$ alkyl, $C_{2-6}$ alkenyl, hydroxy-$C_{1-6}$ alkyl, $C_{1-6}$ alkoxy, $C_{1-6}$ alkoxy-$C_{1-6}$ alkyl; or
(c) $R_9$ and $R_{10}$ taken together with the nitrogen atom to which they are attached form a saturated 3-7 membered heterocyclic ring which may contain a O, S or $NR_{12}$ group, where $R_{12}$ is hydrogen, $C_{1-6}$ alkyl, perhalo-$C_{1-6}$ alkyl, aryl, aryl substituted with one or more groups selected from among $C_{1-6}$ alkyl, halogen, nitro, amino, $C_{1-6}$ alkylamino, perhalo-$C_{1-6}$ alkyl, hydroxy-$C_{1-6}$ alkyl, $C_{1-6}$ alkoxy, $C_{1-6}$ alkoxy-$C_{1-6}$ alkyl and —$COR_{13}$ where $R_{13}$ is hydrogen, $C_{1-6}$ alkyl, perhalo-$C_{1-6}$ alkyl, $C_{1-6}$ alkoxy, aryl, and aryl substituted with one or more of $C_{1-6}$ alkyl, perhalo-$C_{1-6}$ alkyl, hydroxy-$C_{1-6}$ alkyl, or $C_{1-6}$ alkoxy-$C_{1-6}$ alkyl groups;

$R_{110}$-$R_{111}$ are each independently selected from among hydrogen; halo; acyl; alkyl (e.g., $C_{1-6}$ alkyl); substituted alkyl; alkoxy (e.g., $C_{1-6}$ alkoxy); substituted alkoxy; alkenyl; alkynyl; cycloalkyl; hydroxyl; cyano; nitro; azido; amido; hydrazine; amino; substituted amino (e.g., monoalkylamino and dialkylamino); hydroxcarbonyl; alkoxycarbonyl; alkylcarbonyloxy; alkylcarbonylamino; carbamoyloxy; arylsulfonyloxy; alkylsulfonyloxy; —$C(R_{117})$=N—(O)$_j$—$R_{118}$ wherein $R_{117}$ is H, alkyl, alkenyl, cycloalkyl, or aryl, j is 0 or 1, and $R_{118}$ is H, alkyl, alkenyl, cycloalkyl, or heterocycle; and $R_{119}C(O)O$— wherein $R_{119}$ is halogen, amino, substituted amino, heterocycle, substituted heterocycle, or $R_{120}$—O—$(CH_2)_k$— where k is an integer of 1-10 and $R_{120}$ is alkyl, phenyl, substituted phenyl, cycloalkyl, substituted cycloalkyl, heterocycle, or substituted heterocycle; or $R_7$ together with $R_{110}$ or $R_{110}$ together with $R_{111}$ form substituted or unsubstituted methylenedioxy, ethylenedioxy, or ethyleneoxy; and $R_{112}$ is H or OR', wherein R' is alkyl, alkenyl, cycloalkyl, haloalkyl, or hydroxyalkyl.

The aryl groups can be phenyl and naphthyl. Suitable heterocyclic rings when $R_9$ and $R_{10}$ are taken together with the nitrogen atom to which they are attached include: aziridine, azetidine, pyrrolidine, piperidine, hexamethylenimine, imidazolidine, pyrazolidine, isoxazolidine, piperazine, N-methylpiperazine, tetrahydroazepine, N-methyl-tetrahydroazepine, thiazolidine, etc.

In alternative aspects of the invention, the treatment of the present invention includes administering an effective amount of the compounds described herein to a mammal with resistant or refractory cancers showing topoisomerase I mediated resistance or refractory phenomenon.

In yet alternative aspects, the present invention provides methods of treating resistant or refractory cancers associated with radiation therapy alone or radiation therapy in combination with a second chemotherapy. Standard protocols of radiation therapy are well known in the art and thus, the combination therapy using the compounds described herein can be done without undue experimentation.

In still another aspect, the treatment of the present invention includes administering an effective amount of the compounds described herein alone or in combination, simultaneously or sequentially, with a second chemotherapeutic agent. The multi-arm polymeric prodrugs of 7-ethyl-10-hydroxycamptothecin can be administered concurrently with the chemotherapeutic agent or after the administration of the chemotherapeutic agent. Thus, the compounds employed in the present invention can be administered during or after treatment of the second chemotherapeutic agent.

For example, a non-limiting list of the second chemotherapeutic agents includes:

(i) DNA topoisomerase inhibitor: adriamycin, amsacrine, camptothecin, CPT-11, daunorubicin, dactinomycin, doxorubicin, eniposide, epirubicin, etoposide, idarubicin, or mitoxantrone;

(ii) microtubule inhibiting drug, such as a taxane, including paclitaxel, docetaxel, vincristin, vinblastin, nocodazole, epothilones and navelbine;

(iii) DNA damaging agent: actinomycin, amsacrine, anthracyclines, bleomycin, busulfan, camptothecin, carboplatin, chlorambucil, cisplatin, cyclophosphamide, cytoxan, dactinomycin, daunorubicin, docetaxel, doxorubicin, epirubicin, hexamethylmelamineoxaliplatin, iphosphamide, melphalan, merchlorehtamine, mitomycin, mitoxantrone, nitrosourea, plicamycin, procarbazine, taxol, taxotere, teniposide, triethylenethiophosphoramide or etoposide (VP16);

(iv) antimetabolite: folate antagonist; and (v) nucleoside analog: 5-fluorouracil; cytosine arabinoside, azacitidine, 6-mercaptopurine, azathioprine; 5-iodo-2'-deoxyuridine; 6-thioguanine, 2-deoxycoformycin, cladribine, cytarabine, fludarabine, mercaptopurine, thioguanine, pentostatin, AZT (zidovudine), ACV, valacylovir, famiciclovir, acyclovir, cidofovir, penciclovir, ganciclovir, Ribavirin, ddC, ddI (zalcitabine), lamuvidine, Abacavir, Adefovir, Didanosine, d4T (stavudine), 3TC, BW 1592, PMEA/bis-POM PMEA, ddT, HPMPC, HPMPG, HPMPA, PMEA, PMEG, dOTC; DAPD, Ara-AC, pentostatin, dihydro-5-azacytidine, tiazofurin, sangivamycin, Ara-A (vidarabine), 6-MMPR, 5-FUDR (floxuridine), cytarabine (Ara-C; cytosine arabinoside), 5-azacytidine (azacitidine), HBG [9-(4-hydroxybutyl)guanine], (1S,4R)-4-[2-amino-6-cyclopropyl-amino)-9H-purin-9-yl]-2-cyclopentene-1-m-ethanol succinate ("159U89"), uridine, thymidine, idoxuridine, 3-deazauridine, cyclocytidine, dihydro-5-azacytidine, tricirubine, ribavirin, fludrabine, Acyclovir, 1-beta-D-arabinofuranosyl-E-5-(2-bromovinyl)uracil, 2'-fluorocarbocyclic-2'-deoxyguanosine; 6'-fluorocarbocyclic-2'-deoxyguanosine; 1-(beta-D-arabinofuranosyl)-5(E)-(2-iodovinyl)uracil; {(1r-1alpha,2beta,3alpha)-2-amino-9-(2,3-bis(hydroxymethyl) cyclobut-yl)-6H-purin-6-one} Lobucavir, 9H-purin-2-amine, 9-((2-(1-methylethoxy)-1-(1-methylethoxy)-methyl) ethoxy)methyl)-(9Cl); trifluorothymidine, 9→(1,3-dihydroxy-2-propoxy)-methylguanine (ganciclovir), 5-ethyl-2'-deoxyuridine; E-5-(2-bromovinyl)-2'-deoxyuridine; 5-(2-chloroethyl)-2'-deoxyuridine, buciclovir, 6-deoxyacyclovir; 9-(4-hydroxy-3-hydroxymethylbut-1-yl) guanine, E-5-(2-iodovinyl)-2'-deoxyuridine, 5-vinyl-1-β-D-arabinofuranosyluracil, 1-β-D-arabinofuranosylthymine; 2'-nor-2'deoxyguanosine; and 1-β-D-arabinofuranosyladenine.

Other potential anti-cancer agents are selected from altretamine, aminoglutethimide, amsacrine, anastrozole, asparaginase, bcg, bicalutamide, bleomycin, buserelin, busulfan, calcium folinate, campothecin, capecitabine, carboplatin, carmustine, chlorambucil, cisplatin, cladribine, clodronate, colchicine, crisantaspase, cyclophosphamide, cyproterone, cytarabine, dacarbazine, dactinomycin, daunorubicin, dienestrol, diethylstilbestrol, docetaxel, doxorubicin, epirubicin, estradiol, estramustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine. Other numerous anti-cancer agents are listed in US Patent Publication No. 2006/0135468, the contents of which are incorporated herein by reference. As will be appreciated by those of ordinary skill, the amount and protocol for delivering the second chemotherapeutic agent can vary greatly depending upon the condition being treated and the recognized acceptable amounts and dosing of the secondary chemotherapeutic agents. The range of dosage for such secondary agents does not require undue experimentation for successful implementation by the artisan of ordinary skill.

In certain embodiment of the present invention, the treatment of resistant or refractory cancers uses the compounds among:

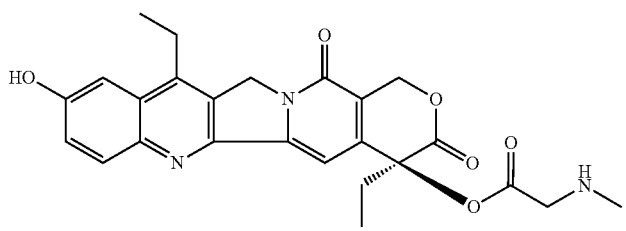

-continued
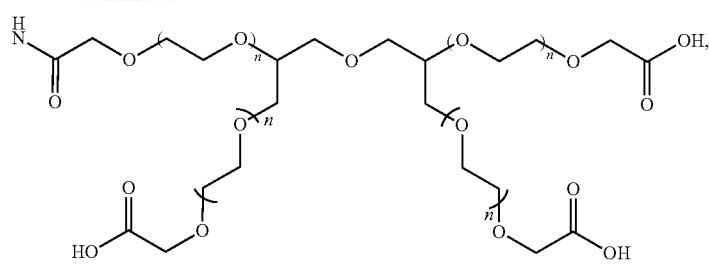
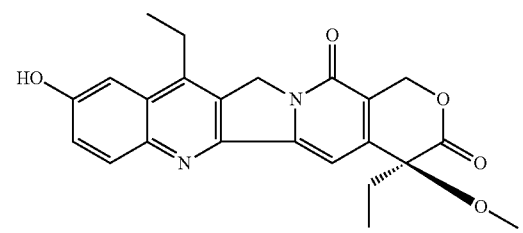
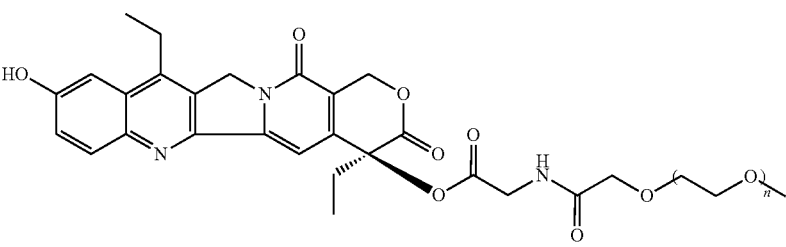
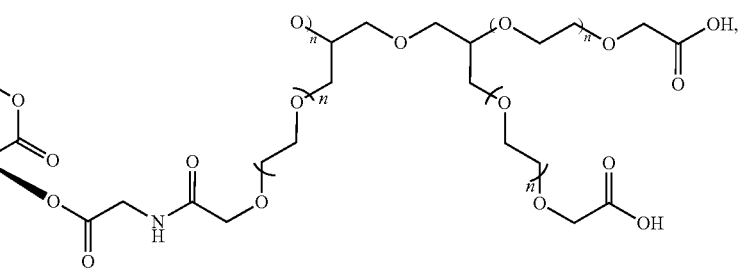
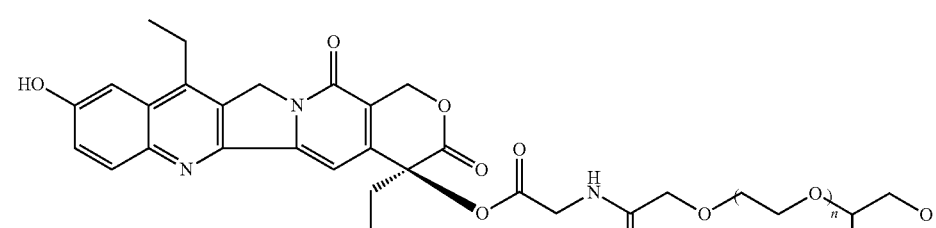
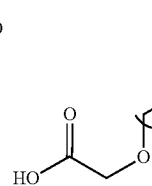

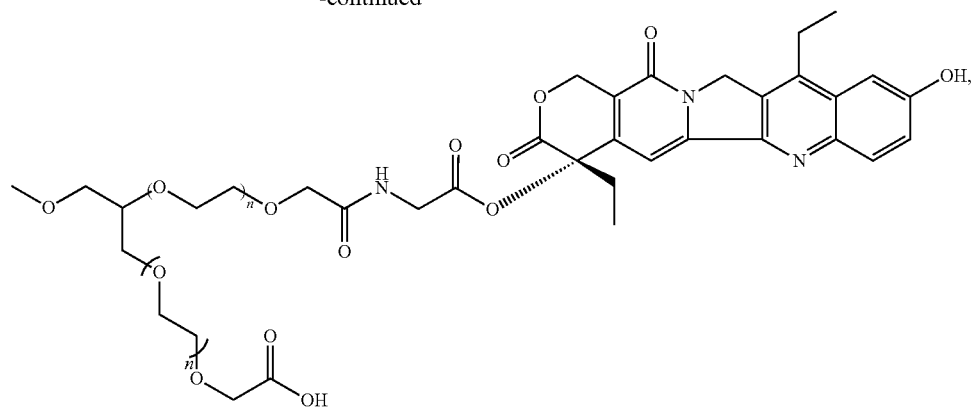
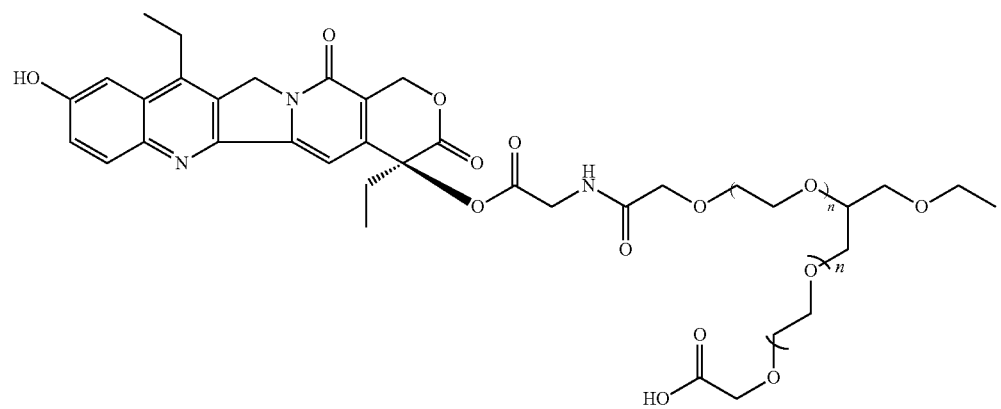
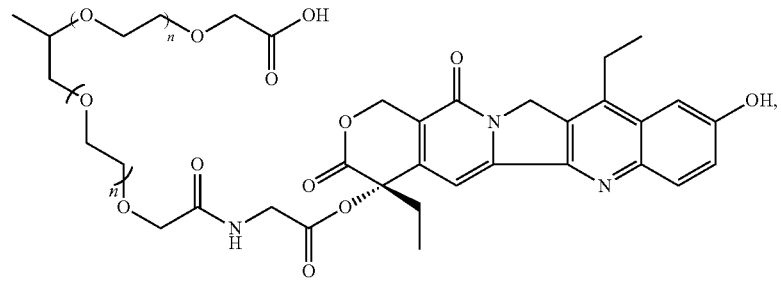
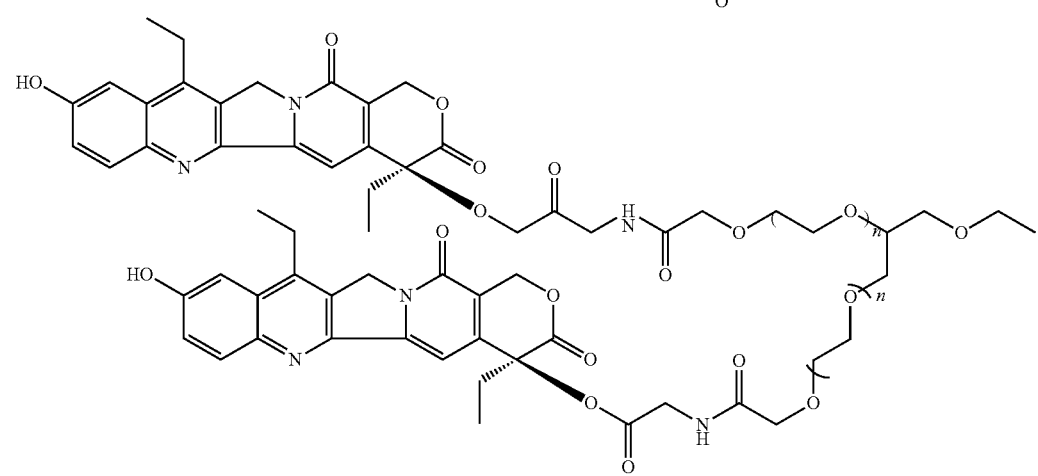

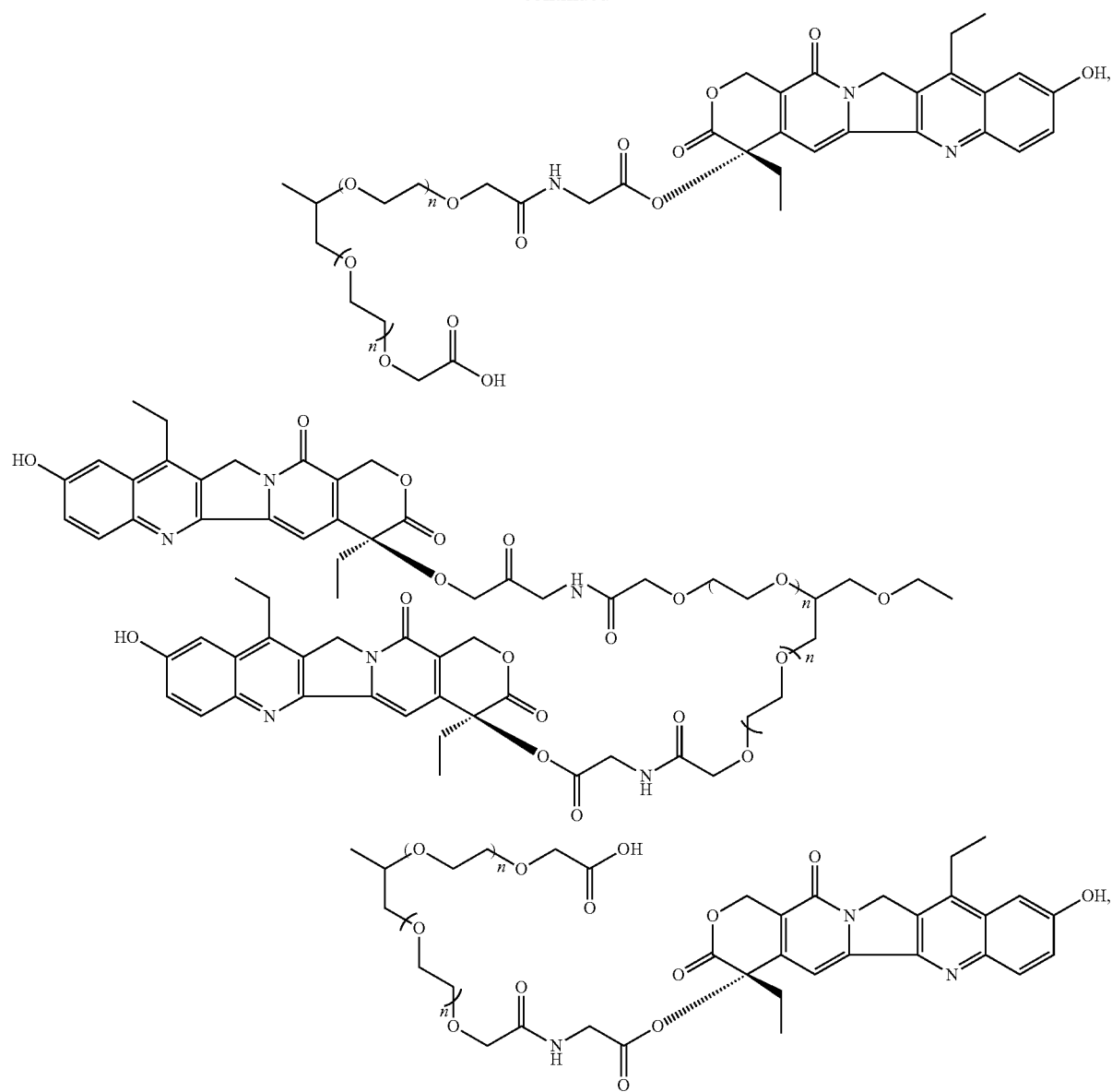
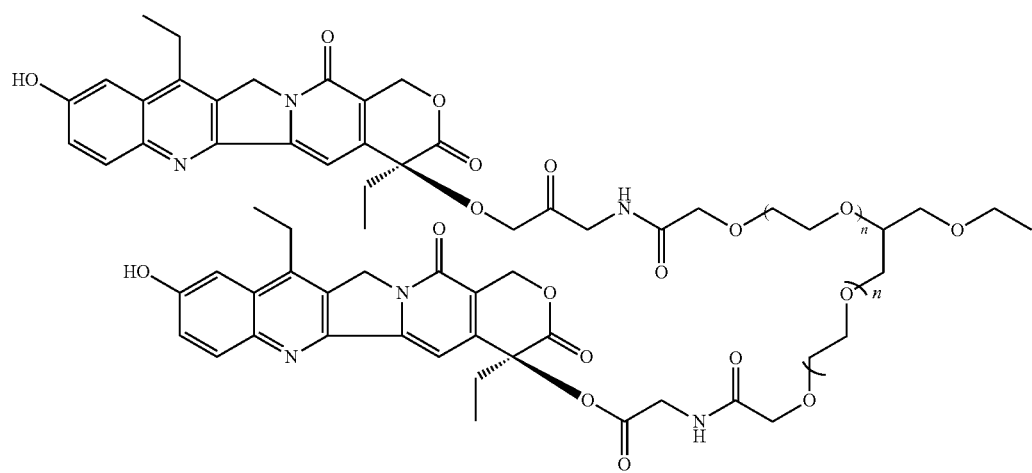
and

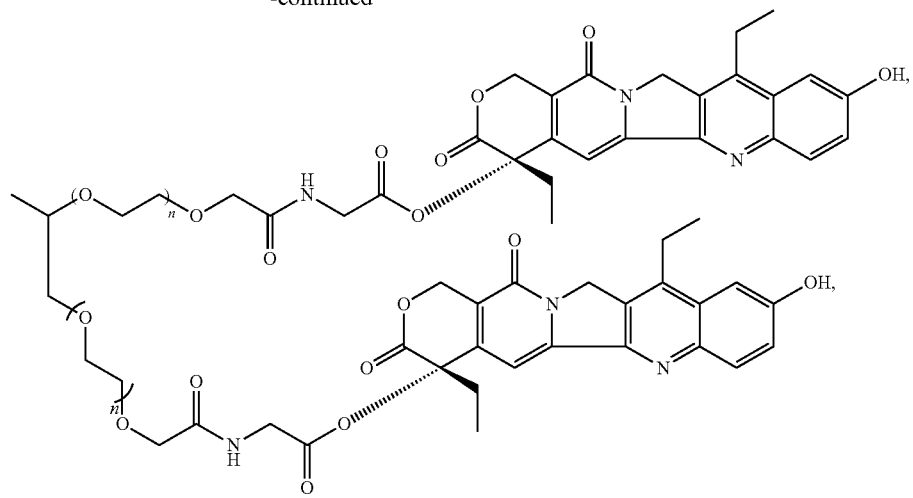
One particularly preferred compound is
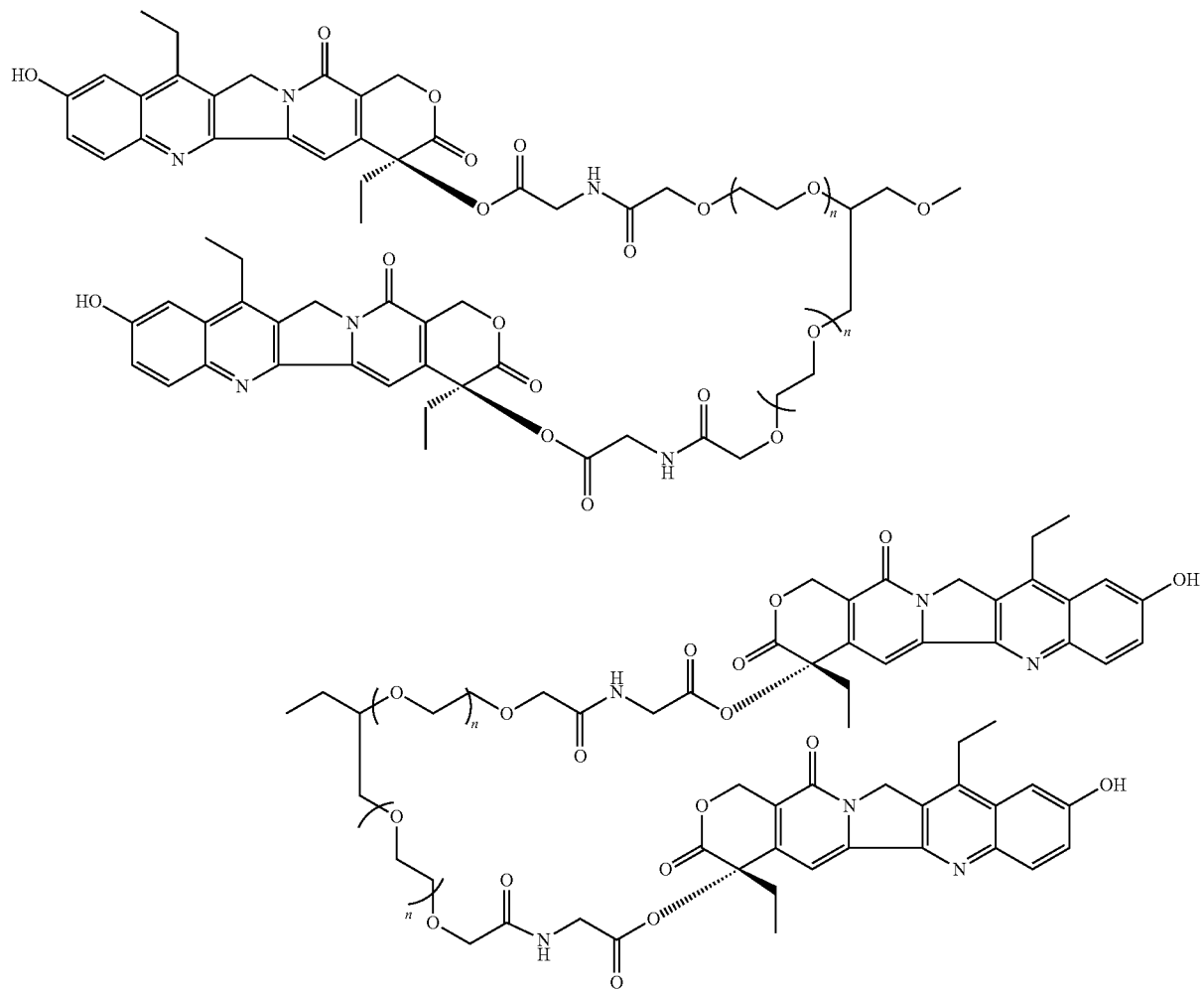
wherein all four arms of the polymer are conjugated to 7-ethyl-10-hydroxycamptothecin through glycine and n is from about 28 to about 341, preferably from about 114 to about 227, or more preferably about 227. One preferred embodiment (compound 9) of the present invention has a molecular weight of about 40,000 da and have the structure of:

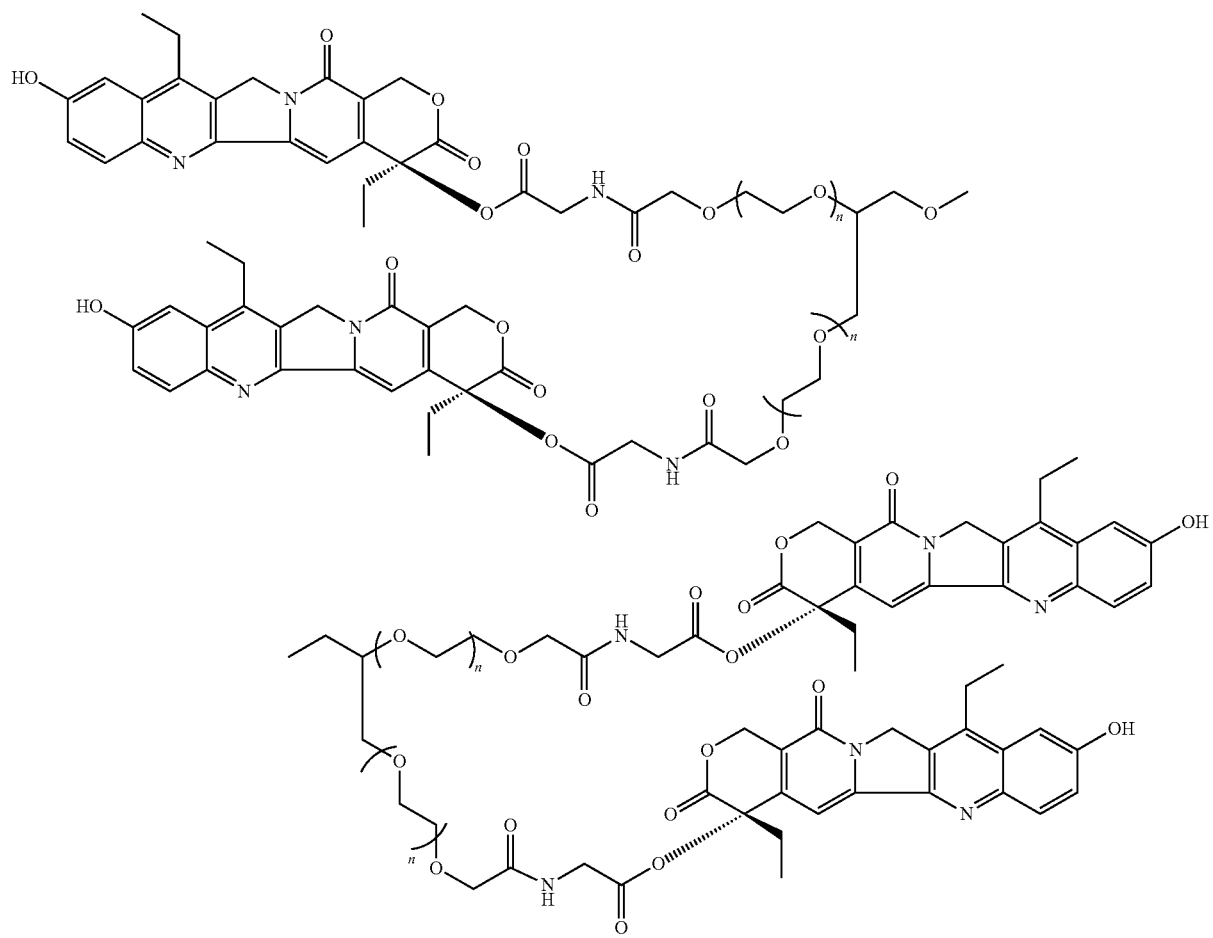

Without being bound by any theory, it is believed that the unexpected efficacy of the methods described herein in treatment of CPT-11 refractory tumors can be attributed, at least in part, to the favorable pharmacokinetic and biodistribution properties of the polymeric compounds described herein. The unexpected efficacy of the compounds described herein can also be based in part on a novel mechanism of action for the drug in vivo. It has been reported that topotecan, another TOP1 inhibitor, inhibits hypoxia-inducible factor (HIF)-1α, leading to marked decrease of angiogenesis and significant tumor growth inhibition. Consistent with this observation, it is believed that the inventive treatment induces a decrease in HIF-1α in cells, which then accumulate the compounds described herein due to an EPR effect in CPT-11 refractory (or sensitive) tumors. However, it is believed that CPT-11 fails to induce a decrease in HIF-1α in CPT-11 refractory tumors, leading to even more angiogenesis. In this aspect, treatment of highly vascular tumors can benefit from accumulation of the inventive compounds described herein due to enhanced EPR effects.

It has also been reported that CPT-11 resistant tumors may have lower levels of TOP1, since low levels of TOP1 have been linked to CPT-11 resistance in tissue culture. The polymeric ester derivatives of 7-ethyl-10-hyroxycamptothecin according to the therapy described herein can also provide higher exposure of 7-ethyl-10-hyroxycamptothecin to cells in vivo than CPT-11. Drug concentrations can be sufficient to kill cells even with low levels of TOP1. Alternatively, variable levels of carboxylesterase can be another contributing factor to CPT-11 resistance, and this enzyme is not required for release of 7-ethyl-10-hyroxycamptothecin from the polymeric ester derivatives of 7-ethyl-10-hyroxycamptothecin conjugates described herein.

B. Multi-Arm Polymeric Conjugates of 7-Ethyl-10-Hydroxycamptothecin

1. Multi-Arm Polymers

The polymeric prodrugs of 7-ethyl-10-hydroxycamptothecin include four-arm PEG attached to 20-OH group of 7-ethyl-10-hydroxycamptothecin through a bifunctional linker. In one aspect of the present invention, the polymeric prodrugs of 7-ethyl-10-hydroxycamptothecin include four-arm PEG, prior to conjugation, having the following structure of

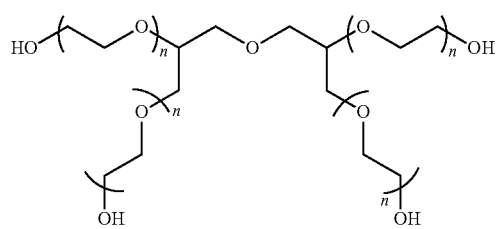

wherein n is a positive integer.

The polymers are those described in NOF Corp. Drug Delivery System catalog, Ver. 8, April 2006, the disclosure of which is incorporated herein by reference.

In one preferred embodiment of the invention, the degree of polymerization for the polymer (n) is from about 28 to about 341 to provide polymers having a total molecular weight of from about 5,000 Da to about 60,000 Da, and preferably from about 114 to about 227 to provide polymers having a total molecular weight of from 20,000 Da to 40,000 Da. (n) represents the number of repeating units in the polymer chain and is dependent on the molecular weight of the polymer. In one particularly preferred embodiment of the invention, n is about 227 to provide the polymeric portion having a total molecular weight of about 40,000 Da.

2. Bifunctional Linkers

In certain aspects of the present invention, L is a residue of an amino acid. The amino acid can be selected from any of the known naturally-occurring L-amino acids, e.g., alanine, valine, leucine, isoleucine, glycine, serine, threonine, methionine, cysteine, phenylalanine, tyrosine, tryptophan, aspartic acid, glutamic acid, lysine, arginine, histidine, proline, and/or a combination thereof to name but a few. In alternative aspects, L can be a peptide residue. The peptide can range in size, for instance, from about 2 to about 10 amino acid residues.

Derivatives and analogs of the naturally occurring amino acids, as well as various art-known non-naturally occurring amino acids (D or L), hydrophobic or non-hydrophobic, are also contemplated to be within the scope of the invention. Simply by way of example, amino acid analogs and derivates include:

2-aminoadipic acid, 3-aminoadipic acid, beta-alanine, beta-aminopropionic acid, 2-aminobutyric acid, 4-aminobutyric acid, piperidinic acid, 6-aminocaproic acid, 2-aminoheptanoic acid, 2-aminoisobutyric acid, 3-aminoisobutyric acid, 2-aminopimelic acid, 2,4-aminobutyric acid, desmosine, 2,2-diaminopimelic acid, 2,3-diaminopropionic acid, n-ethylglycine, N-ethylasparagine, 3-hydroxyproline, 4-hydroxyproline, isodesmosine, allo-isoleucine, N-methylglycine or sarcosine, N-methyl-isoleucine, 6-N-methyllysine, N-methylvaline, norvaline, norleucine, ornithine, and others too numerous to mention, that are listed in 63 Fed. Reg., 29620, 29622, incorporated by reference herein. Some preferred L groups include glycine, alanine, methionine or sarcosine residues. For example, the compounds can be among:

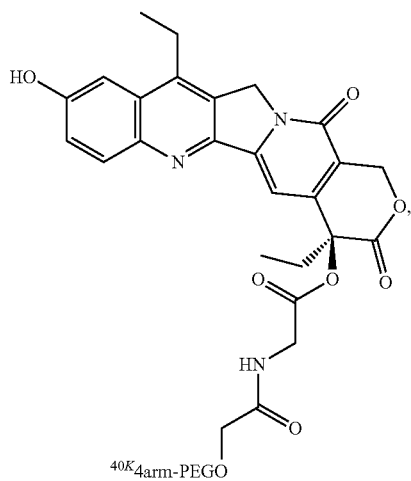

40K4arm-PEGO

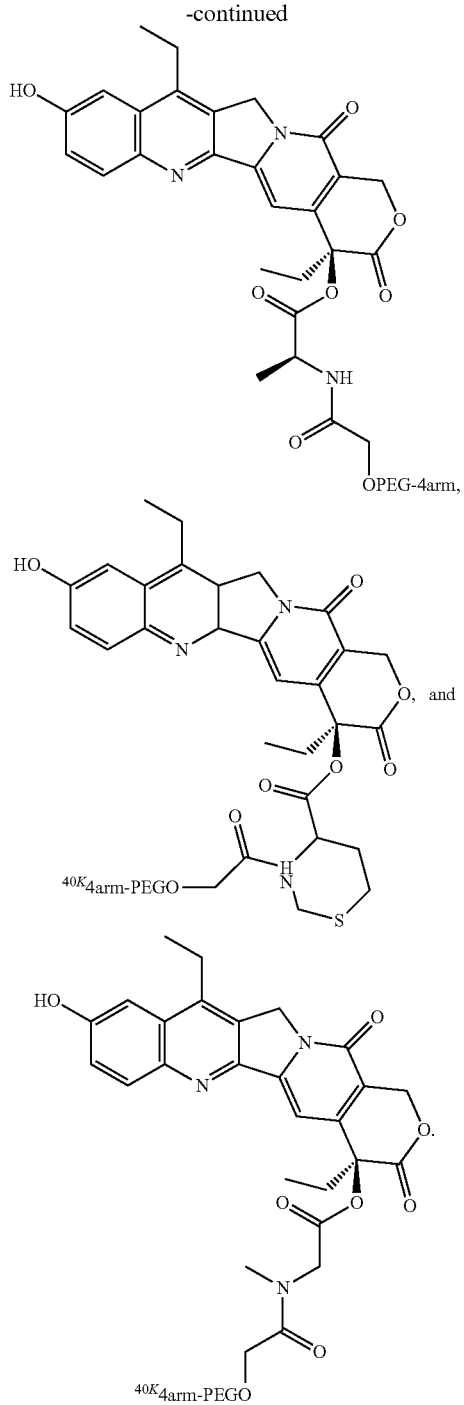

For ease of the description and not limitation, one arm of the four-arm PEG is shown. One arm, up to four arms of the four-arm PEG can be conjugated with 7-ethyl-10-hydroxy-camptothecin.

More preferably, compounds of the present invention include a glycine residue as the linker group (L).

Alternatively, L after attachment between the camptothecin analog and polymer is selected among:

—[C(=O)]$_v$(CR$_{22}$R$_{23}$)$_t$—,
—[C(=O)]$_v$(CR$_{22}$R$_{23}$)$_t$—O—,
—[C(=O)]$_v$(CR$_{22}$R$_{23}$)$_t$—NR$_{26}$—,
—[C(=O)]$_v$O(CR$_{22}$R$_{23}$)$_t$—,

—[C(=O)]$_v$O(CR$_{22}$R$_{23}$)$_t$O—,
—[C(=O)]$_v$O(CR$_{22}$R$_{23}$)$_t$NR$_{26}$—,
—[C(=O)]$_v$NR$_{21}$(CR$_{22}$R$_{23}$)$_t$—,
—[C(=O)]$_v$NR$_{21}$(CR$_{22}$R$_{23}$)$_t$O—,
—[C(=O)]$_v$NR$_{21}$(CR$_{22}$R$_{23}$)$_t$NR$_{26}$—,
—[C(=O)]$_v$(CR$_{22}$R$_{23}$O)$_t$—,
—[C(=O)]$_v$O(CR$_{22}$R$_{23}$O)$_t$—,
—[C(=O)]$_v$NR$_{21}$(CR$_{22}$R$_{23}$O)$_t$—,
—[C(=O)]$_v$(CR$_{22}$R$_{23}$O)$_t$(CR$_{24}$R$_{25}$)$_y$—,
—[C(=O)]$_v$O(CR$_{22}$R$_{23}$O)$_t$(CR$_{24}$R$_{25}$)$_y$—,
—[C(=O)]$_v$NR$_{21}$(CR$_{22}$R$_{23}$O)$_t$(CR$_{24}$R$_{25}$)$_y$—,
—[C(=O)]$_v$(CR$_{22}$R$_{23}$O)$_t$(CR$_{24}$R$_{25}$)$_y$O—,
—[C(=O)]$_v$(CR$_{22}$R$_{23}$)$_t$(CR$_{24}$R$_{25}$O)$_y$—,
—[C(=O)]$_v$O(CR$_{22}$R$_{23}$)$_t$(CR$_{24}$R$_{25}$)$_y$O—,
—[C(=O)]$_v$O(CR$_{22}$R$_{23}$)$_t$(CR$_{24}$R$_{25}$O)$_y$—,
—[C(=O)]$_v$NR$_{21}$(CR$_{22}$R$_{23}$O)$_t$(CR$_{24}$R$_{25}$)$_y$O—,
—[C(=O)]$_v$NR$_{21}$(CR$_{22}$R$_{23}$)$_t$(CR$_{24}$R$_{25}$)$_y$—,
—[C(=O)]$_v$(CR$_{22}$R$_{23}$)$_t$O—(CR$_{28}$R$_{29}$)$_{t'}$—,
—[C(=O)]$_v$(CR$_{22}$R$_{23}$)$_t$NR$_{26}$—(CR$_{28}$R$_{29}$)$_{t'}$—,
—[C(=O)]$_v$(CR$_{22}$R$_{23}$)$_t$S—(CR$_{28}$R$_{29}$)$_{t'}$—,
—[C(=O)]$_v$O(CR$_{22}$R$_{23}$)$_t$O—(CR$_{28}$R$_{29}$)$_{t'}$—,
—[C(=O)]$_v$O(CR$_{22}$R$_{23}$)$_t$NR$_{26}$—(CR$_{28}$R$_{29}$)$_{t'}$—,
—[C(=O)]$_v$O(CR$_{22}$R$_{23}$)$_t$S—(CR$_{28}$R$_{29}$)$_{t'}$—,
—[C(=O)]$_v$NR$_{21}$(CR$_{22}$R$_{23}$)$_t$O—(CR$_{28}$R$_{29}$)$_{t'}$—,
—[C(=O)]$_v$NR$_{21}$(CR$_{22}$R$_{23}$)$_t$NR$_{26}$—(CR$_{28}$R$_{29}$)$_{t'}$—,
—[C(=O)]$_v$NR$_{21}$(CR$_{22}$R$_{23}$)$_t$S—(CR$_{28}$R$_{29}$)$_{t'}$—,
—[C(=O)]$_v$(CR$_{22}$R$_{23}$CR$_{28}$R$_{29}$O)$_t$NR$_{26}$—,
—[C(=O)]$_v$(CR$_{22}$R$_{23}$CR$_{28}$R$_{29}$O)$_t$—,
—[C(=O)]$_v$O(CR$_{22}$R$_{23}$CR$_{28}$R$_{29}$O)$_t$NR$_{26}$—,
—[C(=O)]$_v$O(CR$_{22}$R$_{23}$CR$_{28}$R$_{29}$O)$_t$—,
—[C(=O)]$_v$NR$_{21}$(CR$_{22}$R$_{23}$CR$_{28}$R$_{29}$O)$_t$NR$_{26}$—,
—[C(=O)]$_v$NR$_{21}$(CR$_{22}$R$_{23}$CR$_{28}$R$_{29}$O)$_t$—,
—[C(=O)]$_v$(CR$_{22}$R$_{23}$CR$_{28}$R$_{29}$O)$_t$(CR$_{24}$R$_{25}$)$_y$—,
—[C(=O)]$_v$O(CR$_{22}$R$_{23}$CR$_{28}$R$_{29}$O)$_t$(CR$_{24}$R$_{25}$)$_y$—,
—[C(=O)]$_v$NR$_{21}$(CR$_{22}$R$_{23}$CR$_{28}$R$_{29}$O)$_t$(CR$_{24}$R$_{25}$)$_y$—,
—[C(=O)]$_v$(CR$_{22}$R$_{23}$CR$_{28}$R$_{29}$O)$_t$(CR$_{24}$R$_{25}$)$_y$O—,
—[C(=O)]$_v$(CR$_{22}$R$_{23}$)$_t$(CR$_{24}$R$_{25}$CR$_{28}$R$_{29}$O)$_y$—,
—[C(=O)]$_v$(CR$_{22}$R$_{23}$)$_t$(CR$_{24}$R$_{25}$CR$_{28}$R$_{29}$O)$_y$NR$_{26}$—,
—[C(=O)]$_v$O(CR$_{22}$R$_{23}$CR$_{28}$R$_{29}$O)$_t$(CR$_{24}$R$_{25}$)$_y$O—,
—[C(=O)]$_v$O(CR$_{22}$R$_{23}$)$_t$(CR$_{24}$R$_{25}$CR$_{28}$R$_{29}$O)$_y$—,
—[C(=O)]$_v$O(CR$_{22}$R$_{23}$)$_t$(CR$_{24}$CR$_{25}$CR$_{28}$R$_{29}$O)$_y$NR$_{26}$—,
—[C(=O)]$_v$NR$_{21}$(CR$_{22}$R$_{23}$CR$_{28}$R$_{29}$O)$_t$(CR$_{24}$R$_{25}$)$_y$O—,
—[C(=O)]$_v$NR$_{21}$(CR$_{22}$R$_{23}$)$_t$(CR$_{24}$R$_{25}$CR$_{28}$R$_{29}$O)$_y$—,
—[C(=O)]$_v$NR$_{21}$(CR$_{22}$R$_{23}$)$_t$(CR$_{24}$R$_{25}$CR$_{28}$R$_{29}$O)$_y$NR$_{26}$—,

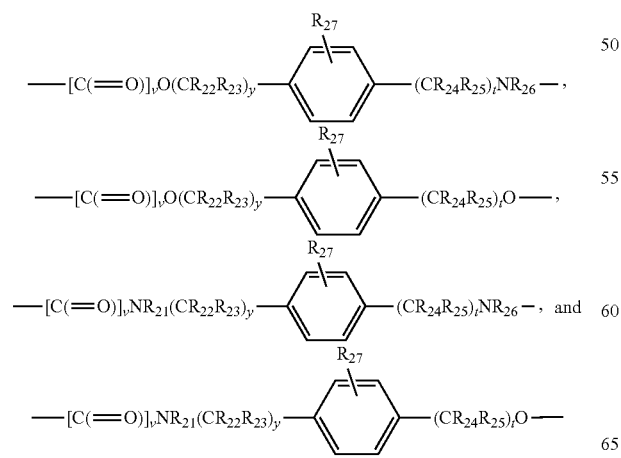

wherein:

$R_{21}$-$R_{29}$ are independently selected among hydrogen, amino, substituted amino, azido, carboxy, cyano, halo, hydroxyl, nitro, silyl ether, sulfonyl, mercapto, $C_{1-6}$ alkylmercapto, arylmercapto, substituted arylmercapto, substituted $C_{1-6}$ alkylthio, $C_{1-6}$ alkyls, $C_{2-6}$ alkenyl, $C_{2-6}$ alkynyl, $C_{3-19}$ branched alkyl, $C_{3-8}$ cycloalkyl, $C_{1-6}$ substituted alkyl, $C_{2-6}$ substituted alkenyl, $C_{2-6}$ substituted alkynyl, $C_{3-8}$ substituted cycloalkyl, aryl, substituted aryl, heteroaryl, substituted heteroaryl, $C_{1-6}$ heteroalkyl, substituted $C_{1-6}$ heteroalkyl, $C_{1-6}$ alkoxy, aryloxy, $C_{1-6}$ heteroalkoxy, heteroaryloxy, $C_{2-6}$ alkanoyl, arylcarbonyl, $C_{2-6}$ alkoxycarbonyl, aryloxycarbonyl, $C_{2-6}$ alkanoyloxy, arylcarbonyloxy, $C_{2-6}$ substituted alkanoyl, substituted arylcarbonyl, $C_{2-6}$ substituted alkanoyloxy, substituted aryloxycarbonyl, $C_{2-6}$ substituted alkanoyloxy, substituted and arylcarbonyloxy;

(t), (t') and (y) are independently selected from zero or a positive integer, preferably from about 1 to about 10; and (v) is 0 or 1.

In some preferred embodiments, L can include:

—[C(=O)]$_v$(CH$_2$)$_t$—,
—[C(=O)]$_v$(CH$_2$)$_t$—O—,
—[C(=O)]$_v$(CH$_2$)$_t$—NR$_{26}$—,
—[C(=O)]$_v$O(CH$_2$)$_t$—,
—[C(=O)]$_v$O(CH$_2$)$_t$O—,
—[C(=O)]$_v$O(CH$_2$)$_t$NH—,
—[C(=O)]$_v$NH(CH$_2$)$_t$—,
—[C(=O)]$_v$NH(CH$_2$)$_t$O—,
—[C(=O)]$_v$NH(CH$_2$)$_t$NH—,
—[C(=O)]$_v$(CH$_2$O)$_t$—,
—[C(=O)]$_v$O(CH$_2$O)$_t$—,
—[C(=O)]$_v$NH(CH$_2$O)$_t$—,
—[C(=O)]$_v$(CH$_2$O)$_t$(CH$_2$)$_y$—,
—[C(=O)]$_v$O(CH$_2$O)$_t$H$_2$)$_y$—,
—[C(=O)]$_v$NH(CH$_2$O)$_t$(CH$_{25}$)$_y$—,
—[C(=O)]$_v$(CH$_2$O)$_t$(CH$_2$)$_y$O—,
—[C(=O)]$_v$(CH$_2$)$_t$(CH$_2$O)$_y$—,
—[C(=O)]$_v$O(CH$_2$O)$_t$(CH$_2$)$_y$O—,
—[C(=O)]$_v$O(CH$_2$)$_t$(CH$_2$O)$_y$—,
—[C(=O)]$_v$NH(CH$_2$O)$_t$(CH$_2$)$_y$O—,
—[C(=O)]$_v$NH(CR$_{22}$R$_{23}$)$_t$(CH$_2$O)$_y$—,
—[C(=O)]$_v$(CH$_2$)$_t$O—(CH$_2$)$_{t'}$—,
—[C(=O)]$_v$(CH$_2$)$_t$NH—(CH$_2$)$_{t'}$—,
—[C(=O)]$_v$(CH$_2$)$_t$S—(CH$_2$)$_{t'}$—,
—[C(=O)]$_v$O(CH$_2$)$_t$O—(CH$_2$)$_{t'}$—,
—[C(=O)]$_v$O(CH$_2$)$_t$NH—(CH$_2$)$_{t'}$—,
—[C(=O)]$_v$O(CH$_2$)$_t$S—(CH$_2$)$_{t'}$—,
—[C(=O)]$_v$NH(CR$_{22}$R$_{23}$)$_t$O—(CH$_2$)$_{t'}$—,
—[C(=O)]$_v$NH(CH$_2$)$_t$NH—(CH$_2$)$_{t'}$—,
—[C(=O)]$_v$NH(CH$_2$)$_t$S—(CH$_2$)$_{t'}$—,
—[C(=O)]$_v$(CH$_2$CH$_2$O)$_t$NR$_{26}$—,
—[C(=O)]$_v$(CH$_2$CH$_2$O)$_t$—,
—[C(=O)]$_v$O(CH$_2$CH$_2$O)$_t$NH—,
—[C(=O)]$_v$O(CH$_2$CH$_2$O)$_t$—,
—[C(=O)]$_v$NH(CH$_2$CH$_2$O)$_t$NH—,
—[C(=O)]$_v$NH(CH$_2$CH$_2$O)$_t$—,
—[C(=O)]$_v$(CH$_2$CH$_2$O)$_t$(CH$_2$)$_y$—,
—[C(=O)]$_v$O(CH$_2$CH$_2$O)$_t$(CH$_2$)$_y$—,
—[C(=O)]$_v$NH(CH$_2$CH$_2$O)$_t$(CH$_2$)$_y$—,
—[C(=O)]$_v$(CH$_2$CH$_2$O)$_t$(CH$_2$)$_y$O—,
—[C(=O)]$_v$(CH$_2$)$_t$(CH$_2$CH$_2$O)$_y$—,
—[C(=O)]$_v$(CH$_2$)$_t$(CH$_2$CH$_2$O)$_y$NH—,
—[C(=O)]$_v$O(CH$_2$CH$_2$O)$_t$(CH$_2$)$_y$O—,
—[C(=O)]$_v$O(CH$_2$)$_t$(CH$_2$CH$_2$O)$_y$—,
—[C(=O)]$_v$O(CH$_2$)$_t$(CH$_2$CH$_2$O)$_y$NH—,
—[C(=O)]$_v$NH(CH$_2$CH$_2$O)$_t$(CH$_2$)$_y$O—,

—[C(=O)]$_v$NH(CH$_2$)$_t$(CH$_2$CH$_2$O)$_y$—,
—[C(=O)]$_v$NH(CH$_2$)$_t$(CH$_2$CH$_2$O)$_y$NH—,

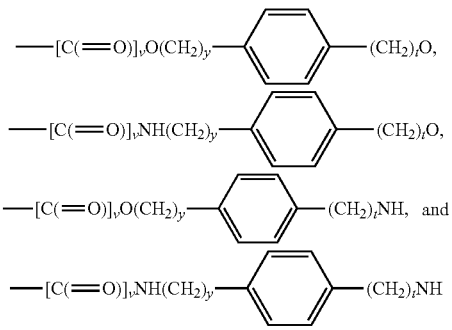

wherein (t), (t') and (y) are independently selected from zero or a positive integer, preferably from about 1 to about 10; and (v) is 0 or 1.

In some aspects of the present invention, the compounds include from 1 to about 10 units of the bifunctional linker. In some preferred aspects of the present invention, the compounds include one unit of the bifunctional linker and thus m is 1.

Additional linkers are found in Table 1 of Greenwald et al. (*Bioorganic & Medicinal Chemistry*, 1998, 6:551-562), the contents of which are incorporated by reference herein.

C. Synthesis of Prodrugs

Generally, the polymeric 7-ethyl-10-hydroxycamptothecin prodrugs described herein are prepared by reacting one or more equivalents of an activated multi-arm polymer with, for example, one or more equivalents per active site of amino acid-(20)-7-ethyl-10-hydroxycamptothecin compound under conditions which are sufficient to effectively cause the amino group to undergo a reaction with the carboxylic acid of the polymer and form a linkage. Details of the synthesis are described in U.S. patent application Ser. No. 11/704,607 entitled "Multi-arm Polymeric Conjugates of 7-Ethyl-10-hydroxycamptothecin For Treatment of Breast, Colorectal, Pancreatic, Ovarian and Lung Cancers", the contents of which are incorporated herein by reference in its entirety. HPLC analysis of compounds made in accordance with the methods of synthesis showed that on average, four 7-ethyl-10-hydroxycamptothecin molecules are conjugated to one four-arm PEG molecule (4% by weight).

D. Compositions/Formulations

Pharmaceutical compositions containing the polymer conjugates of the present invention may be manufactured by processes well known in the art, e.g., using a variety of well-known mixing, dissolving, granulating, levigating, emulsifying, encapsulating, entrapping or lyophilizing processes. The compositions may be formulated in conjunction with one or more physiologically acceptable carriers comprising excipients and auxiliaries which facilitate processing of the active compounds into preparations which can be used pharmaceutically. Proper formulation is dependent upon the route of administration chosen. Parenteral routes are preferred in many aspects of the invention.

For injection, including, without limitation, intravenous, intrausclular and subcutaneous injection, the compounds of the invention may be formulated in aqueous solutions, preferably in physiologically compatible buffers such as physiological saline buffer or polar solvents including, without limitation, a pyrrolidone or dimethylsulfoxide.

The compounds are preferably formulated for parenteral administration, e.g., by bolus injection or continuous infusion. Formulations for injection may be presented in unit dosage form, e.g., in ampoules or in multi-dose containers. Useful compositions include, without limitation, suspensions, solutions or emulsions in oily or aqueous vehicles, and may contain adjuncts such as suspending, stabilizing and/or dispersing agents. Pharmaceutical compositions for parenteral administration include aqueous solutions of a water soluble form, such as, without limitation, a salt of the active compound. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes. Aqueous injection suspensions may contain substances that increase the viscosity of the suspension, such as sodium carboxymethyl cellulose, sorbitol, or dextran. Optionally, the suspension may also contain suitable stabilizers and/or agents that increase the solubility of the compounds to allow for the preparation of highly concentrated solutions. Alternatively, the active ingredient may be in powder form for constitution with a suitable vehicle, e.g., sterile, pyrogen-free water, before use.

For oral administration, the compounds can be formulated by combining the active compounds with pharmaceutically acceptable carriers well-known in the art. Such carriers enable the compounds of the invention to be formulated as tablets, pills, lozenges, dragees, capsules, liquids, gels, syrups, pastes, slurries, solutions, suspensions, concentrated solutions and suspensions for diluting in the drinking water of a patient, premixes for dilution in the feed of a patient, and the like, for oral ingestion by a patient. Pharmaceutical preparations for oral use can be made using a solid excipient, optionally grinding the resulting mixture, and processing the mixture of granules, after adding other suitable auxiliaries if desired, to obtain tablets or dragee cores. Useful excipients are, in particular, fillers such as sugars, including lactose, sucrose, mannitol, or sorbitol, cellulose preparations such as, for example, maize starch, wheat starch, rice starch and potato starch and other materials such as gelatin, gum tragacanth, methyl cellulose, hydroxypropyl-methylcellulose, sodium carboxy-methylcellulose, and/or polyvinylpyrrolidone (PVP). If desired, disintegrating agents may be added, such as cross-linked polyvinyl pyrrolidone, agar, or alginic acid. A salt such as sodium alginate may also be used.

For administration by inhalation, the compounds of the present invention can conveniently be delivered in the form of an aerosol spray using a pressurized pack or a nebulizer and a suitable propellant.

The compounds may also be formulated in rectal compositions such as suppositories or retention enemas, using, e.g., conventional suppository bases such as cocoa butter or other glycerides.

In addition to the formulations described previously, the compounds may also be formulated as depot preparations. Such long acting formulations may be administered by implantation (for example, subcutaneously or intramuscularly) or by intramuscular injection. The compounds of this invention may be formulated for this route of administration with suitable polymeric or hydrophobic materials (for instance, in an emulsion with a pharmacologically acceptable oil), with ion exchange resins, or as a sparingly soluble derivative such as, without limitation, a sparingly soluble salt.

Additionally, the compounds may be delivered using a sustained-release system, such as semi-permeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the particular compound, additional stabilization strategies may be employed.

Other delivery systems such as liposomes and emulsions can also be used.

E. Dosages

A therapeutically effective amount refers to an amount of compound effective to prevent, alleviate or ameliorate the resistance or refractory phenomenon to anti-cancer agents such as camptothecin or related analog, for example, CPT-11. Determination of a therapeutically effective amount is well within the capability of those skilled in the art, especially in light of the disclosure herein.

For any compound used in the methods of the invention, the therapeutically effective amount can be estimated initially from in vitro assays. Then, the dosage can be formulated for use in animal models so as to achieve a circulating concentration range that includes the effective dosage. Such information can then be used to more accurately determine dosages useful in patients.

The amount of the composition, e.g., used as a prodrug, that is administered will depend upon the parent molecule included therein. Generally, the amount of prodrug used in the treatment methods is that amount which effectively achieves the desired therapeutic result in mammals. Naturally, the dosages of the various prodrug compounds can vary somewhat depending upon the parent compound, rate of in vivo hydrolysis, molecular weight of the polymer, etc. In addition, the dosage, of course, can vary depending upon the dosage form and route of administration.

In general, however, the polymeric ester derivatives of 7-ethyl-10-hyroxycamptothecin described herein can be administered in amounts ranging from about 0.1 to about 30 mg/kg/dose and preferably about 0.2 to about 10 mg/kg/dose, yet preferably from about 0.6 to about 6 mg/kg/dose for systemic delivery.

The range set forth above is illustrative and those skilled in the art will determine the optimal dosing of the prodrug selected based on clinical experience and the treatment indication. Moreover, the exact formulation, route of administration and dosage can be selected by the individual physician in view of the patient's condition. Additionally, toxicity and therapeutic efficacy of the compounds described herein can be determined by standard pharmaceutical procedures in cell cultures or experimental animals using methods well-known in the art.

In one embodiment, the treatment of the present invention includes administering the compounds described herein in an amount of from about 0.3 to about 6 mg/kg/dose to a mammal having resistant or refractory cancers to such as CPT and CPT-11 therapies.

Alternatively and preferably, the amounts of the compounds administered can be based on body surface of human or other mammals. Thus, the treatment of the present invention includes administering the compounds described herein in an amount of from about 0.1 to about 45 mg/m$^2$ body surface/dose. Preferably, the amounts of the compounds described herein range from about 0.2 to about 25 mg/m$^2$ body surface/dose. Some preferred doses include one of the following: 1.25, 2.0 2.5, 3.3, 5, 10, and 16.5 mg/m$^2$/dose. Preferably, the amounts administered can range from about 1.25 to about 16.5 mg/m$^2$ body surface/dose. Alternatively, they can be from about 2.5 to about 13 mg/m$^2$ body surface/dose or from about 2 to about 5 mg/m$^2$ body surface/dose.

The treatment protocol can be based on a single dose administered once every three weeks or divided into multiple doses which are given as part of a multi-week treatment protocol. Thus, the treatment regimens can include one dose every three weeks for each treatment cycle and, alternatively one dose weekly for three weeks followed by one week off for each cycle.

The precise dose will depend on the stage and severity of the condition, and the individual characteristics of the patient being treated, as will be appreciated by one of ordinary skill in the art. It is also contemplated that the treatment continues until satisfactory results are observed, which can be as soon as after 1 cycle although from about 3 to about 6 cycles or more cycles may be required.

In some preferred embodiments, the treatment protocol includes administering the amount ranging from about 1.25 to about 16.5 mg/m$^2$ body surface/dose every three weeks repeating for about 3 cycles or more. The amount administered per each cycle can range more preferably from about 2.5 to about 16.5 mg/m$^2$ body surface/dose. Alternatively, the compounds described herein can be administered weekly for three weeks, followed by one week without treatment and repeating for about 3 cycles or more until the desired results are observed.

In one particular embodiment, the polymeric ester derivatives of 7-ethyl-10-hydroxycamptothecin can be administered one dose such as 10 mg/m$^2$ every three weeks in treatment of colon cancer. The dosage of treatment cycle can be designed as an escalating dose regimen when two or more treatment cycles are applied. The polymeric drug is preferably administered via IV infusion.

In all aspects of the invention where polymeric conjugates are administered, the dosage amount mentioned is based on the amount of 7-ethyl-10-hydroxycamptothecin rather than the amount of polymeric conjugate administered. It is contemplated that the treatment will be given for one or more cycles until the desired clinical result is obtained. The exact amount, frequency and period of administration of the compound of the present invention will vary, of course, depending upon the sex, age and medical condition of the patient as well as the severity of the disease as determined by the attending clinician.

Still further aspects include combining the therapy described herein with other anticancer therapies for synergistic or additive benefit. In one particular embodiment, the compounds described herein can be administered in combination with Erbitux® (cetuximab). 400 mg/m$^2$ Erbitux® plus the compounds described herein can be administered as an initial dose followed by 250 mg/m$^2$ weekly until disease progresses. Details of Erbitux® dosage information are described in the package insert, the contents of which are incorporated herein.

EXAMPLES

The following examples serve to provide further appreciation of the invention but are not meant in any way to restrict the effective scope of the invention.

Example 1

Therapeutic Efficacy of Four-arm PEG-Gly-(7-ethyl-10-hydroxy-camptothecin) in Human Colorectal Tumor Xenografted Mice Refractory to CPT-11

Therapeutic efficacy of four-arm PET-Gly-(7-ethyl-10-hydroxycamptothecin) against a refractory human HT-29 colorectal tumor grown in nude mice was determined. Human HT-29 colorectal tumors were established in nude mice by subcutaneous injection of 1×10^6 cells/mouse into a right auxiliary flank. When tumors reached an average volume of 100 mm³, mice were treated with CPT-11 (40 mg/kg/dose; q2d×4). Mice were monitored for tumor growth. On day 15, mice with tumors that did not respond to CPT-11 therapy (tumor volume ≧3× initial tumor volume at the start of CPT-11 therapy) were considered CPT-11 refractory. These mice were selected, randomized and divided into two groups. One group was treated with MTD of CPT-11 (40 mg/kg/dose; q2d×5) and the other group was treated with MTD of four-arm $^{40K}$PEG-Gly-(7-ethyl-10-hydroxycamptothecin) (compound 9) (10 mg/kg/dose q2d×5) starting day 16. The drugs were administered intravenously via the tail vein.

The results are set forth in FIG. 1. Tumors continued to grow in the CPT-11 refractory mice further treated with CPT-11. On day 42, tumor volume increased by 255% compared to day 15. In the mice treated with four-arm. $^{40K}$PEG-Gly-(7-ethyl-10-hydroxycamptothecin) (compound 9), tumor volume decreased by 25% compared to day 15 on day 42. 29% and 100% of animals treated with CPT-11 were sacrificed by day 42 and 54 respectively due to excessive tumor burden (>1,650 mm³). In the group treated with four-arm $^{40K}$PEG-Gly-(7-ethyl-10-hydroxycamptothecin), only 1 of 7 animals was sacrificed on day 63. 58% of the mice treated with four-arm $^{40K}$PEG-Gly-(7-ethyl-10-hydroxycamptothecin) had tumors <1,650 mm³ by day 72. The results show that four-arm $^{40K}$PEG-Gly-(7-ethyl-10-hydroxycamptothecin) has therapeutic activity in the treatment of CPT-11 refractory cancer. The data in FIG. 1 represent mean±standard deviation (n=7).

Without being bound by any theory, the therapy using the compounds described herein unexpectedly avoids resistance associated with CPT-11 therapy. The therapy described herein provides ways to treat cancers more effectively by avoiding and reducing potential drug resistance. Patients and clinicians can benefit from unexpected lack of resistance to the compounds described herein as compared to CPT-11 based therapy in treatment of cancer.

Example 2

Therapeutic Efficacy of Four-arm PEG-Gly-(7-ethyl-10-hydroxy-camptothecin) in Human Colorectal Tumor Xenografted Mice Refractory to CPT-11 in the Second Round Treatment Human HT-29 colorectal tumors were established in nude mice by subcutaneous injection of 1×10^6 cells/mouse into a right auxiliary flank. When tumors reached an average volume of 100 mm³, mice were treated with CPT-11 (40 mg/kg/dose; q2d×4). Mice were monitored for tumor growth. On day 15, mice that responded to CPT-11 therapy (mice that had tumor volumes <3× initial tumor volume at the start of CPT-11 therapy, i.e., mice considered CPT-sensitive) were selected, randomized and divided into two groups. One group was further treated with MTD of CPT-11 (40 mg/kg/dose; q2d×5) and the other group was treated with MTD of four-arm $^{40K}$PEG-Gly-(7-ethyl-10-hydroxycamptothecin) (10 mg/kg/dose q2d×5) starting day 16. The drugs were administered intravenously via the tail vein.

Figure 2:
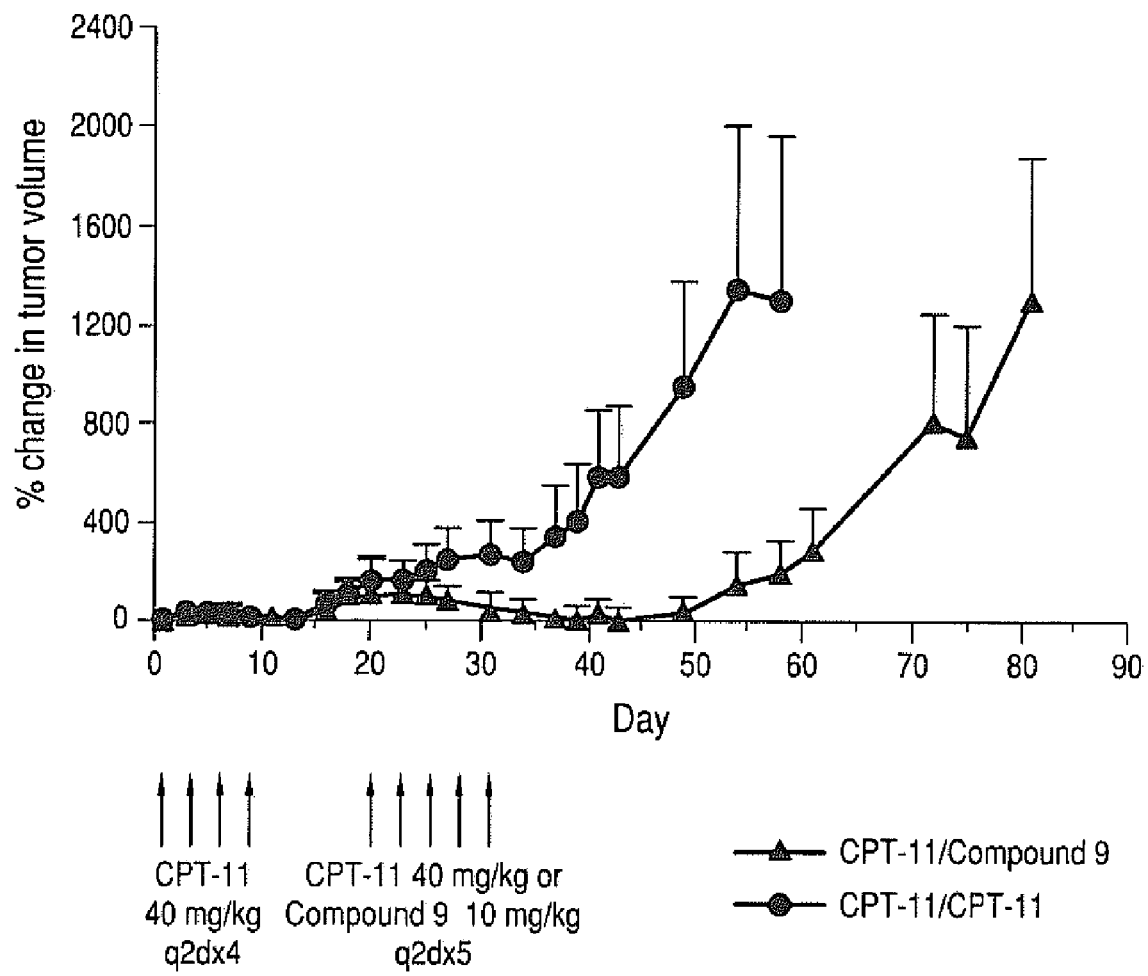
FIG. 2 shows anticancer activity of four-arm PEG-Gly-7-ethyl-10-hydroxycamptothecin in treatment of CPT-11 refractory colorectal tumor as described in Example 2.

The results are set forth in FIG. 2. On day 54, in mice treated with CPT-11, tumor volume increased by 1298% compared to day 1. Mice treated with four-arm $^{40K}$PEG-Gly-(7-ethyl-10-hydroxycamptothecin) had tumor volume moderately increased by 193%. Additionally, as of day 61, 60% animals were sacrificed in CPT-11 treated group due to excessive tumor burden. No deaths have been recorded in four-arm $^{40K}$PEG-Gly-(7-ethyl-10-hydroxycamptothecin) (compound 9) treated group on day 61. The results show that four-arm $^{40K}$PEG-Gly-(7-ethyl-10-hydroxycamptothecin) outperformed therapeutic activity of CPT-11 and is significantly effective for second round and subsequent round therapies in the treatment of CPT-11 refractory cancer. The data in FIG. 2 represent mean±standard deviation (n=10).

Example 3

In vitro Cytotoxicity of Four-arm PEG-Gly-(7-ethyl-10-hydroxy-camptothecin) in the CPT Refractory Cell Line CPT-refractory cell line (CEM/C2) and the corresponding non-refractory parent cell line (CEM) were treated with PEG-Gly-(7-ethyl-10-hydroxycamptothecin), 7-ethyl-10-hydroxycamptothecin, and CPT-11. The CEM/C2 and CEM were obtained from NCI. The CEM cell lines are acute lymphoblastic leukemia cell lines. The in vitro cytotoxicity of each drug was determined using a MTS assay. Briefly, cells were placed in 96-well plates (8×10^4 per well) and then treated with serial dilutions of four-arm $^{40K}$PEG-Gly-(7-ethyl-10-hydroxycamptothecin) (compound 9), CPT or free 7-ethyl-10-hydroxycamptothecin for 2 days at 37° C. At the end of the incubation, MTS dye was added and incubated for 2 to 3 hours at 37° C. and formation of a colored product (formazan) was measured at 490 nm. The % viability at each drug concentration was calculated as [OD test samples−background]/[OD controls (no treatment)−background]. Sigmoidal dose response curves were generated by plotting Log (Drug) as a function of % viability (survival) and $IC_{50}$ values were calculated using the GraphPad Prism software.

Figure 3:
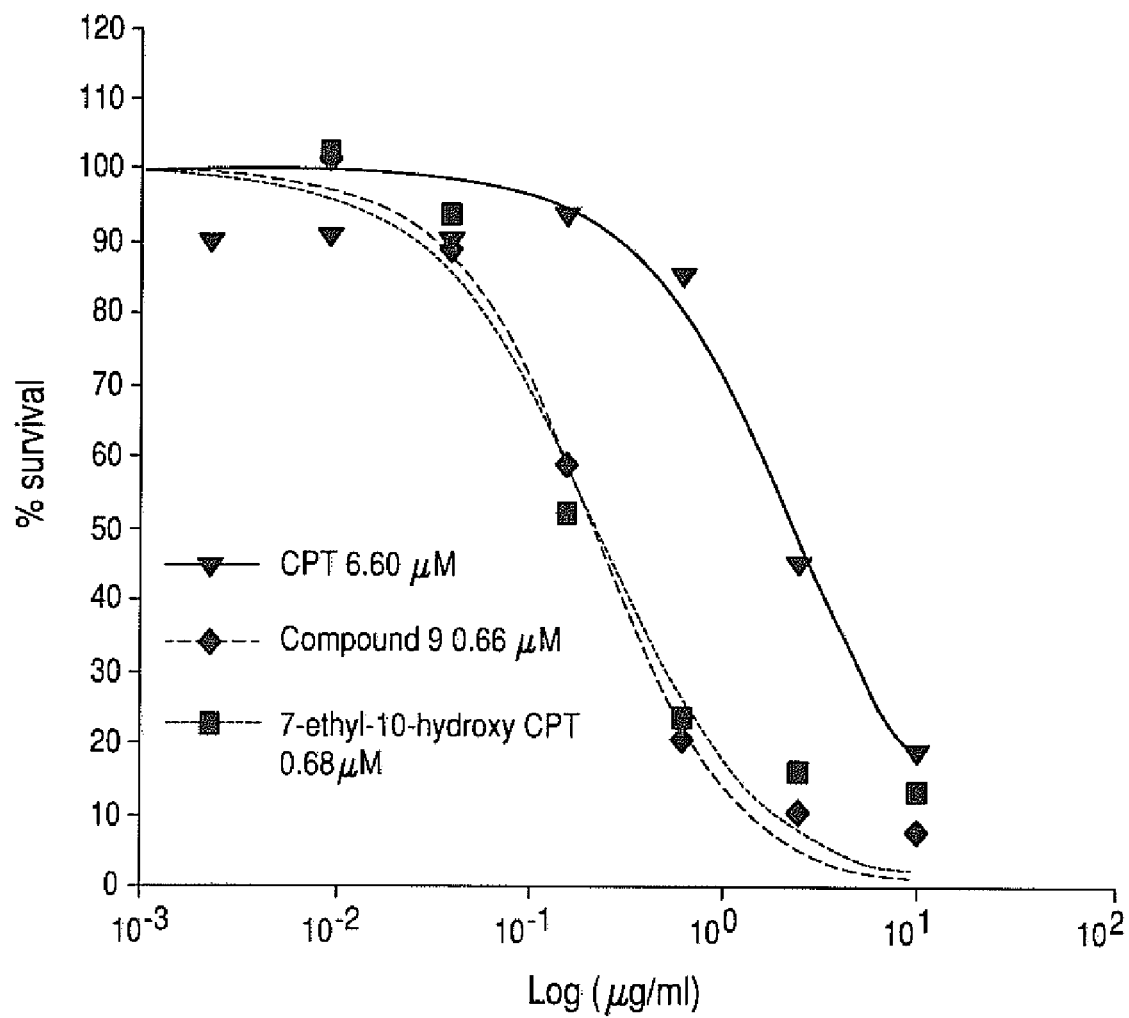
FIG. 3 shows in vitro cytotoxicity of four-arm PEG-Gly-7-ethyl-10-hydroxycamptotehcin in the cells refractory to CPT as described in Example 3.
Figure 4:
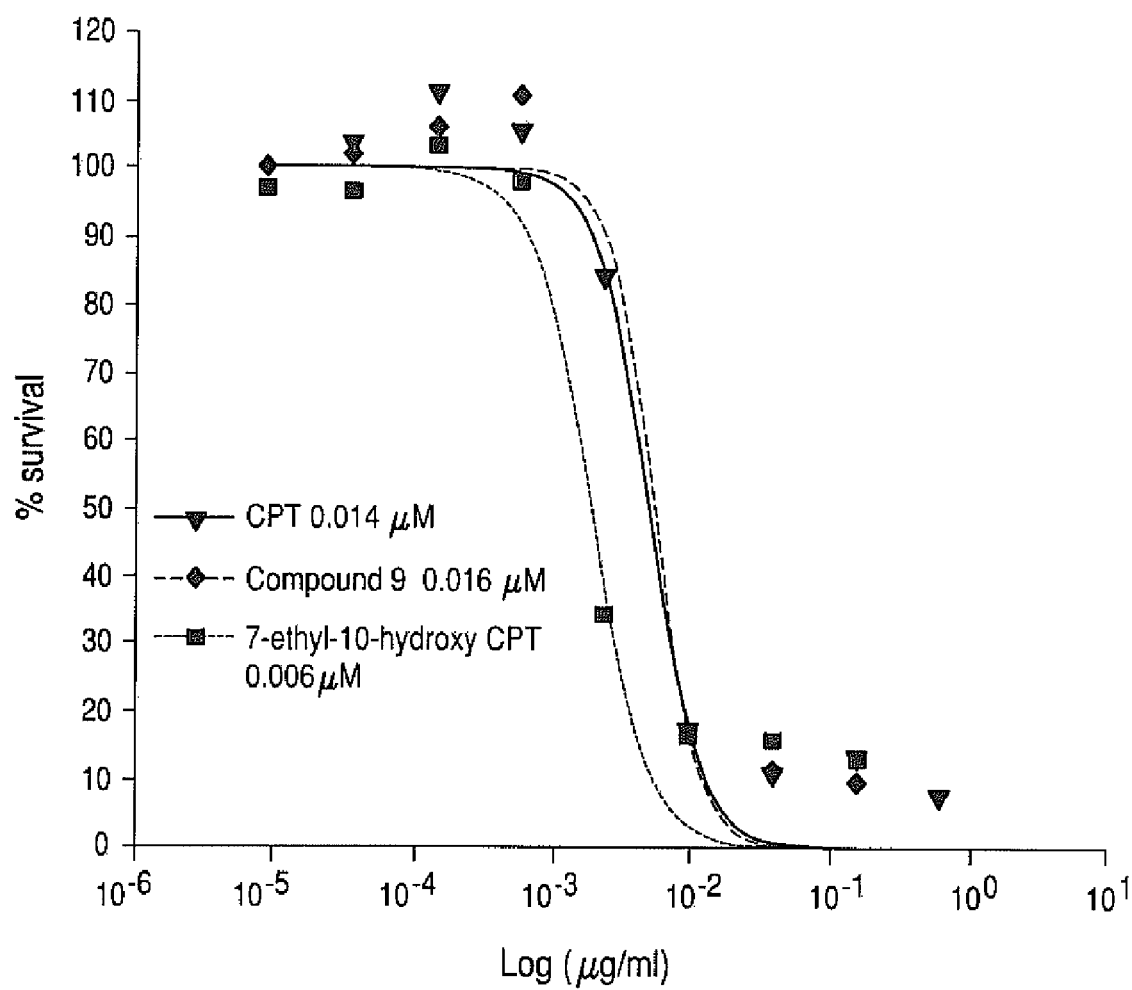
FIG. 4 shows in vitro cytotoxicity of four-arm PEG-Gly-7-ethyl-10-hydroxycamptotehcin in the cells non-refractory to CPT as described in Example 3.

The results are set forth in FIGS. 3 and 4. The cytotoxicity (μM of each compound that results in an $IC_{50}$) shows the in vitro anti-tumor potency of each compound. This study was used to determine the therapeutic effect of four-arm PEG-Gly-(7-ethyl-10-hydroxycamptothecin) in CPT-refractory cancer. The four-arm PEG-Gly-(7-ethyl-10-hydroxy-camptothecin) was about 10 fold more potent than CPT-11 in the acute lymphoblastic leukemia cell line refractory to CPT as shown in FIG. 3. In addition, all four-arm PEG-Gly-(7-ethyl-10-hydroxycamptothecin), CPT-11 and 7-ethyl-10-hydroxy-camptothecin showed similar potency in the parent cell line (CEM) as shown in FIG. 4. The results show that four-arm PEG-Gly-(7-ethyl-10-hydroxycamptothecin) has potency for treating cancers resistant to topoisomerase I inhibitors such as CPT.

We claim:

1. A method of treating a resistant or refractory colorectal cancer in a mammal, comprising:
administering an effective amount of a compound of formula (I):

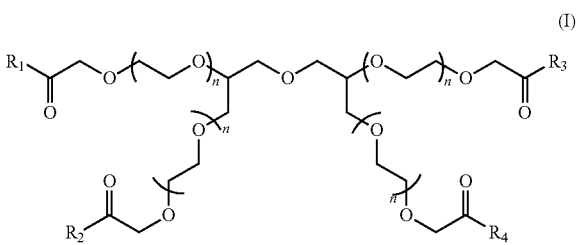

wherein
$R_1$, $R_2$, $R_3$ and $R_4$ are independently OH or

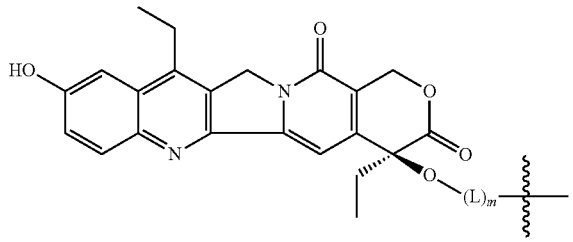

wherein
L is a bifunctional linker;
m is 0 or a positive integer; and
n is a positive integer;
provided that $R_1$, $R_2$, $R_3$ and $R_4$ are not all OH;
or a pharmaceutically acceptable salt thereof to said mammal having a resistant or refractory colorectal cancer.

2. The method of claim 1, wherein the resistant or refractory colorectal cancer includes a solid tumor.

3. The method of claim 1, wherein the resistant or refractory colorectal cancer is metastatic.

4. The method of claim 1, wherein the resistant or refractory colorectal cancer is resistant or refractory to camptothecin or camptothecin analog therapy.

5. The method of claim 1, wherein the resistant or refractory colorectal cancer is resistant or refractory to CPT-11 therapy.

6. The method of claim 1, wherein the resistant or refractory colorectal cancer is resistant or refractory to camptothecin therapy.

7. The method of claim 1, wherein L is a residue of an amino acid or amino acid derivative, and the amino acid derivative is selected from the group consisting of 2-aminoadipic acid, 3-aminoadipic acid, beta-alanine, beta-aminopropionic acid, 2-aminobutyric acid, 4-aminobutyric acid, piperidinic acid, 6-aminocaproic acid, 2-aminoheptanoic acid, 2-aminoisobutyric acid, 3-aminoisobutyric acid, 2-aminopimelic acid, 2,4-aminobutyric acid, desmosine, 2,2-diaminopimelic acid, 2,3-diaminopropionic acid, n-ethylglycine, N-ethylasparagine, 3-hydroxyproline, 4-hydroxyproline, isodesmosine, allo-isoleucine, N-methylglycine, sarcosine, N-methyl-isoleucine, 6-N-methyllysine, N-methylvaline, norvaline, norleucine, and ornithine.

8. The method of claim 7, wherein L is a residue of glycine, alanine, methionine or sarcosine.

9. The method of claim 7, wherein L is a residue of glycine.

10. The method of claim 1, wherein L is selected from the group consisting of

—[C(=O)]$_v$(CR$_{22}$R$_{23}$)$_t$—,
—[C(=O)]$_v$(CR$_{22}$R$_{23}$)$_t$—O—,
—[C(=O)]$_v$(CR$_{22}$R$_{23}$)$_t$—NR$_{26}$—,
—[C(=O)]$_v$O(CR$_{22}$R$_{23}$)$_t$—,
—[C(=O)]$_v$O(CR$_{22}$R$_{23}$)$_t$O—,
—[C(=O)]$_v$O(CR$_{22}$R$_{23}$)$_t$NR$_{26}$—,
—[C(=O)]$_v$NR$_{21}$(CR$_{22}$R$_{23}$)$_t$—,
—[C(=O)]$_v$NR$_{21}$(CR$_{22}$R$_{23}$)$_t$O—,
—[C(=O)]$_v$NR$_{21}$(CR$_{22}$R$_{23}$)$_t$NR$_{26}$—,
—[C(=O)]$_v$(CR$_{22}$R$_{23}$O)$_t$—,
—[C(=O)]$_v$O(CR$_{22}$R$_{23}$O)$_t$—,
—[C(=O)]$_v$NR$_{21}$(CR$_{22}$R$_{23}$O)$_t$—,
—[C(=O)]$_v$(CR$_{22}$R$_{23}$O)$_t$(CR$_{24}$R$_{25}$)$_y$—,
—[C(=O)]$_v$O(CR$_{22}$R$_{23}$O)$_t$(CR$_{24}$R$_{25}$)$_y$—,
—[C(=O)]$_v$NR$_{21}$(CR$_{22}$R$_{23}$O)$_t$(CR$_{24}$R$_{25}$)$_y$—,
—[C(=O)]$_v$(CR$_{22}$R$_{23}$O)$_t$(CR$_{24}$R$_{25}$)$_y$O—,
—[C(=O)]$_v$(CR$_{22}$R$_{23}$)$_t$(CR$_{24}$R$_{25}$O)$_y$—,
—[C(=O)]$_v$O(CR$_{22}$R$_{23}$O)$_t$(CR$_{24}$R$_{25}$)$_y$O—,
—[C(=O)]$_v$O(CR$_{22}$R$_{23}$)$_t$(CR$_{24}$R$_{25}$O)$_y$—,
—[C(=O)]$_v$NR$_{21}$(CR$_{22}$R$_{23}$O)$_t$(CR$_{24}$R$_{25}$)$_y$O—,
—[C(=O)]$_v$NR$_{21}$(CR$_{22}$R$_{23}$)$_t$(CR$_{24}$R$_{25}$O)$_y$—,
—[C(=O)]$_v$(CR$_{22}$R$_{23}$)$_t$O—(CR$_{28}$R$_{29}$)$_{t'}$—,
—[C(=O)]$_v$(CR$_{22}$R$_{23}$)$_t$NR$_{26}$—(CR$_{28}$R$_{29}$)$_{t'}$—,
—[C(=O)]$_v$(CR$_{22}$R$_{23}$)$_t$S—(CR$_{28}$R$_{29}$)$_{t'}$—,
—[C(=O)]$_v$O(CR$_{22}$R$_{23}$)$_t$O—(CR$_{28}$R$_{29}$)$_{t'}$—,
—[C(=O)]$_v$O(CR$_{22}$R$_{23}$)$_t$NR$_{26}$—(CR$_{28}$R$_{29}$)$_{t'}$—,
—[C(=O)]$_v$O(CR$_{22}$R$_{23}$)$_t$S—(CR$_{28}$R$_{29}$)$_{t'}$—,
—[C(=O)]$_v$NR$_{21}$(CR$_{22}$R$_{23}$)$_t$O—(CR$_{28}$R$_{29}$)$_{t'}$—,
—[C(=O)]$_v$NR$_{21}$(CR$_{22}$R$_{23}$)$_t$NR$_{26}$—(CR$_{28}$R$_{29}$)$_{t'}$—,
—[C(=O)]$_v$NR$_{21}$(CR$_{22}$R$_{23}$)$_t$S—(CR$_{28}$R$_{29}$)$_{t'}$—,
—[C(=O)]$_v$(CR$_{22}$R$_{23}$CR$_{28}$R$_{29}$O)$_t$NR$_{26}$—,
—[C(=O)]$_v$(CR$_{22}$R$_{23}$CR$_{28}$R$_{29}$O)$_t$—,
—[C(=O)]$_v$O(CR$_{22}$R$_{23}$CR$_{28}$R$_{29}$O)$_t$NR$_{26}$—,
—[C(=O)]$_v$O(CR$_{22}$R$_{23}$CR$_{28}$R$_{29}$O)$_t$—,
—[C(=O)]$_v$NR$_{21}$(CR$_{22}$R$_{23}$CR$_{28}$R$_{29}$O)$_t$NR$_{26}$—,
—[C(=O)]$_v$NR$_{21}$(CR$_{22}$R$_{23}$CR$_{28}$R$_{29}$O)$_t$—,
—[C(=O)]$_v$(CR$_{22}$R$_{23}$CR$_{28}$R$_{29}$O)$_t$(CR$_{24}$R$_{25}$)$_y$—,
—[C(=O)]$_v$O(CR$_{22}$R$_{23}$CR$_{28}$R$_{29}$O)$_t$(CR$_{24}$R$_{25}$)$_y$—,
—[C(=O)]$_v$NR$_{21}$(CR$_{22}$R$_{23}$CR$_{28}$R$_{29}$O)$_t$(CR$_{24}$R$_{25}$)$_y$—,
—[C(=O)]$_v$(CR$_{22}$R$_{23}$CR$_{28}$R$_{29}$O)$_t$(CR$_{24}$R$_{25}$)$_y$O—,
—[C(=O)]$_v$(CR$_{22}$R$_{23}$)$_t$(CR$_{24}$R$_{25}$CR$_{28}$R$_{29}$O)$_y$—,
—[C(=O)]$_v$(CR$_{22}$R$_{23}$)$_t$(CR$_{24}$R$_{25}$CR$_{28}$R$_{29}$O)$_y$NR$_{26}$—,
—[C(=O)]$_v$O(CR$_{22}$R$_{23}$CR$_{28}$R$_{29}$O)$_t$(CR$_{24}$R$_{25}$)$_y$O—,
—[C(=O)]$_v$O(CR$_{22}$R$_{23}$)$_t$(CR$_{24}$R$_{25}$CR$_{28}$R$_{29}$O)$_y$—,
—[C(=O)]$_v$O(CR$_{22}$R$_{23}$)$_t$(CR$_{24}$R$_{25}$CR$_{28}$R$_{29}$O)$_y$NR$_{26}$—,
—[C(=O)]$_v$NR$_{21}$(CR$_{22}$R$_{23}$CR$_{28}$R$_{29}$O)$_t$(CR$_{24}$R$_{25}$)$_y$O—,
—[C(=O)]$_v$NR$_{21}$(CR$_{22}$R$_{23}$)$_t$(CR$_{24}$R$_{25}$CR$_{28}$R$_{29}$O)$_y$—,
—[C(=O)]$_v$NR$_{21}$(CR$_{22}$R$_{23}$)$_t$(CR$_{24}$R$_{25}$CR$_{28}$R$_{29}$O)$_y$NR$_{26}$—,

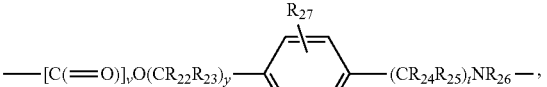

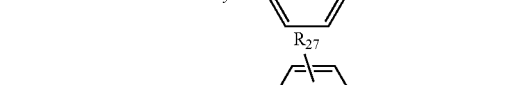

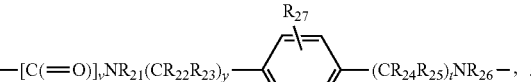

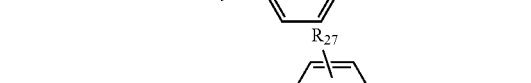

wherein:
$R_{21}$-$R_{29}$ are independently selected from the group consisting of hydrogen, amino, substituted amino, azido, carboxy, cyano, halo, hydroxyl, nitro, silyl ether, sulfonyl, mercapto, $C_{1-6}$ alkylmercapto, arylmercapto, substituted arylmercapto, substituted $C_{1-6}$ alkylthio, $C_{1-6}$ alkyls, $C_{2-6}$ alkenyl, $C_{2-6}$ alkynyl, $C_{3-19}$ branched alkyl, $C_{3-8}$ cycloalkyl, $C_{1-6}$ substituted alkyl, $C_{2-6}$ substituted alkenyl, $C_{2-6}$ substituted alkynyl, $C_{3-8}$ substituted cycloalkyl, aryl, substituted aryl, heteroaryl, substituted heteroaryl, $C_{1-6}$ heteroalkyl, substituted $C_{1-6}$ heteroalkyl, $C_{1-6}$ alkoxy, aryloxy, $C_{1-6}$ heteroalkoxy, heteroaryloxy, $C_{2-6}$ alkanoyl, arylcarbonyl, $C_{2-6}$ alkoxycarbonyl, aryloxycarbonyl, $C_{2-6}$ alkanoyloxy, arylcarbonyloxy, $C_{2-6}$ substituted alkanoyl, substituted arylcarbonyl, $C_{2-6}$ substituted alkanoyloxy, substituted aryloxycarbonyl, $C_{2-6}$ substituted alkanoyloxy, substituted and arylcarbonyloxy;

(t), (t') and (y) are independently selected from zero or a positive integer; and (v) is 0 or 1.

11. The method of claim 1, wherein m is from about 1 to about 10.

12. The method of claim 1, wherein m is about 1.

13. The method of claim 1, wherein n is from about 28 to about 341 so that the total molecular weight of the polymeric portion of the compound of formula (I) ranges from about 5,000 to about 60,000 daltons.

14. The method of claim 1, wherein n is from about 114 to about 227 so that the total molecular weight of the polymeric portion of the compound of formula (I) ranges from about 20,000 to about 40,000 daltons.

15. The method of claim 1, wherein n is about 227 so that the total molecular weight of the polymeric portion of the compound of formula (I) is about 40,000 daltons.

16. The method of claim 1, wherein the compound of formula (I) is part of a pharmaceutical composition and $R_1$, $R_2$, $R_3$ and $R_4$ are all

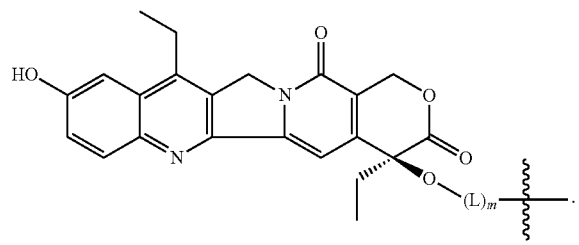

17. A method of claim 1, wherein the compound of formula (I) is selected from the group consisting of

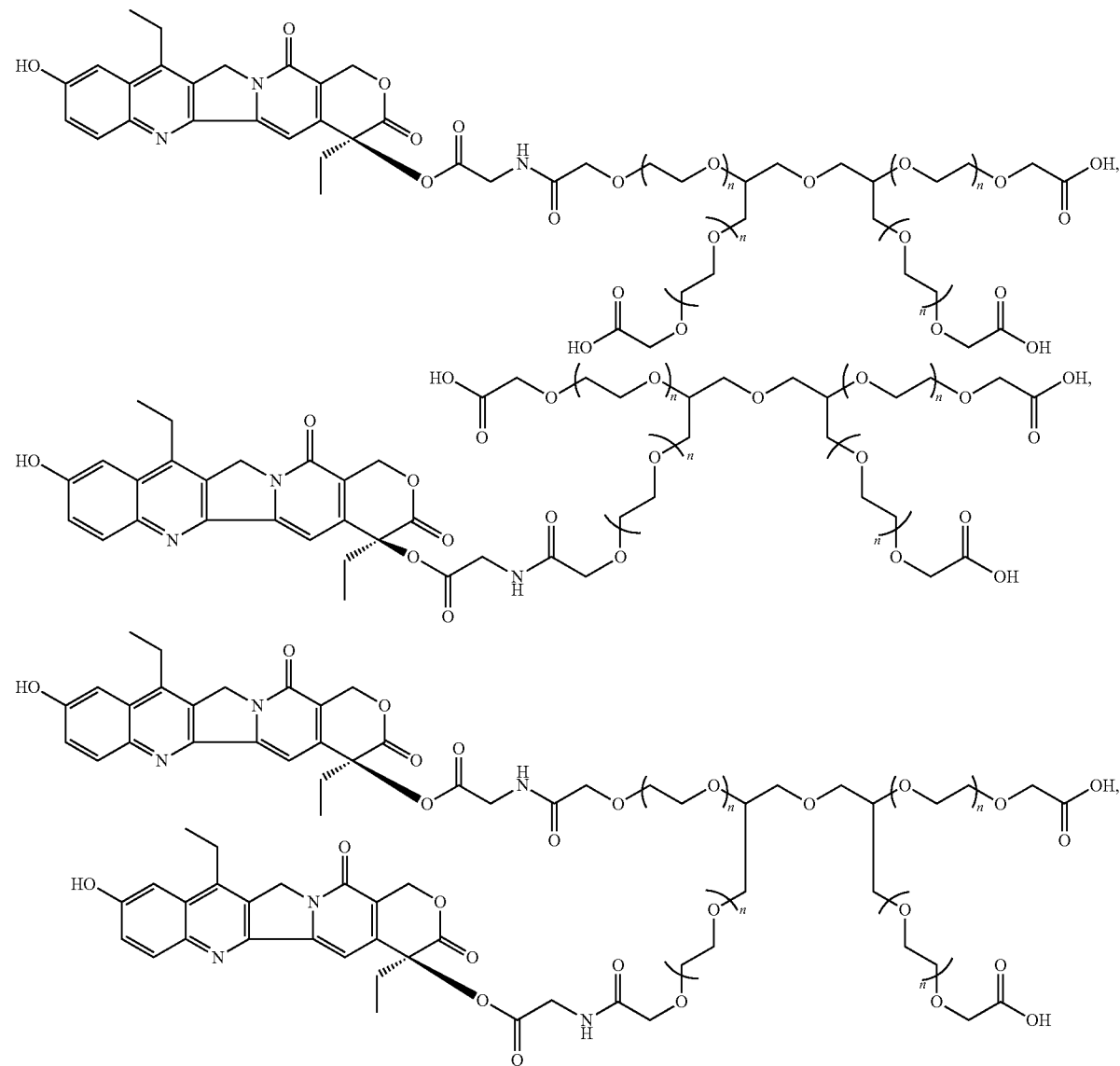

-continued
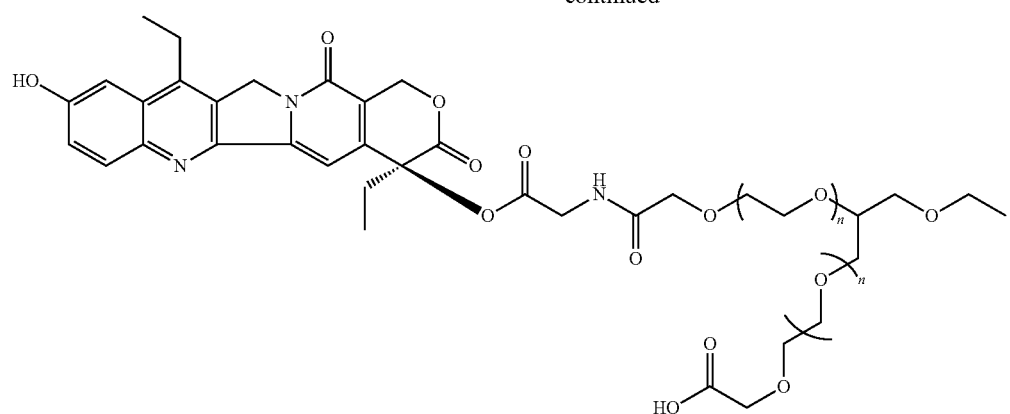
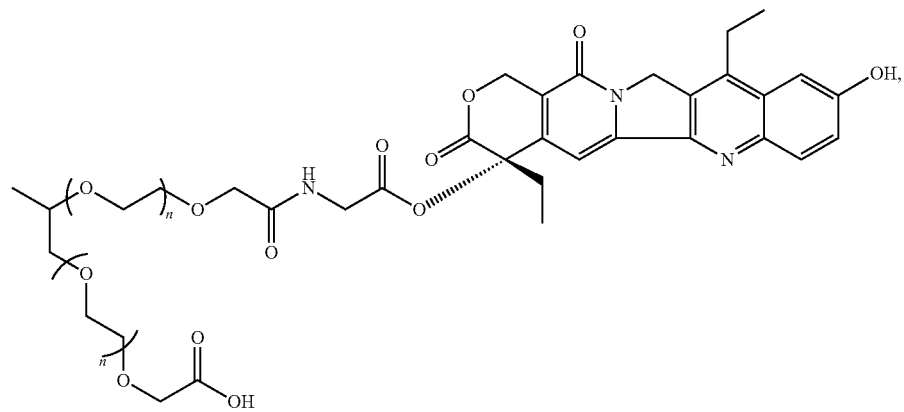
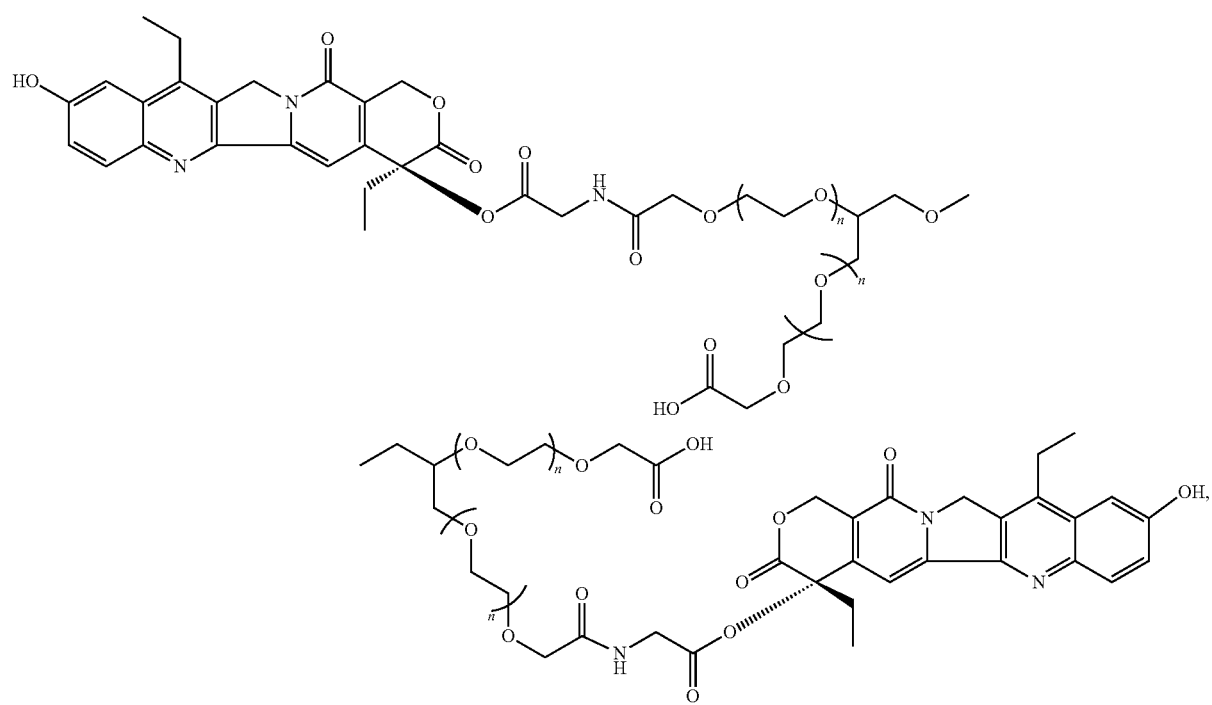

-continued
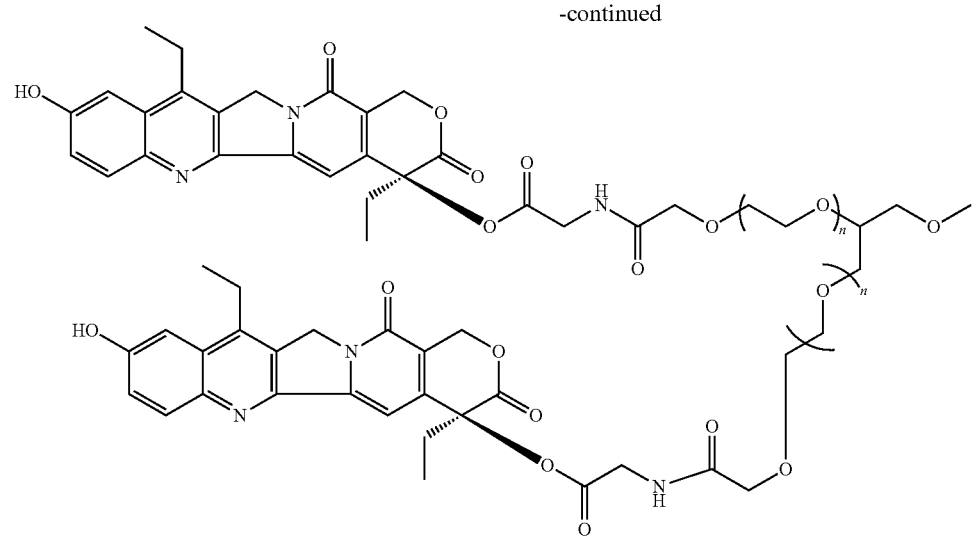
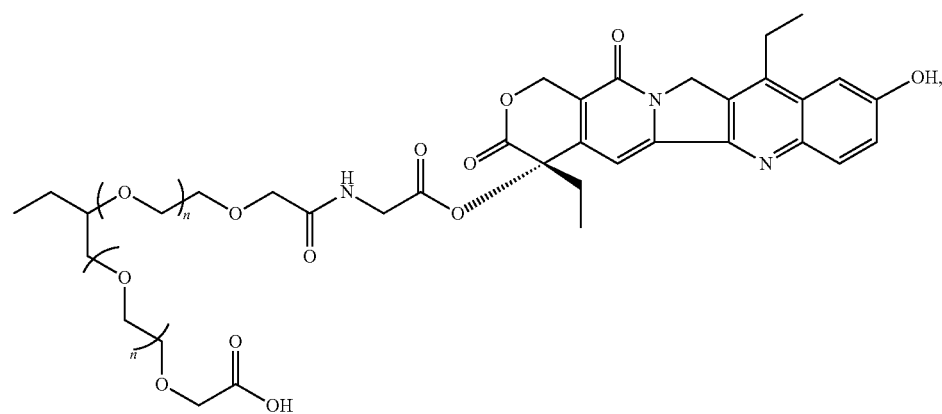
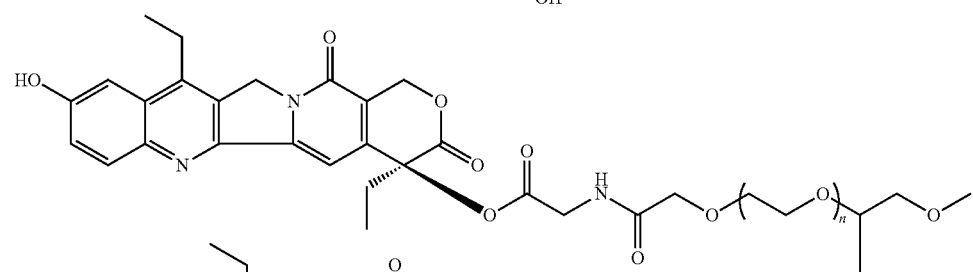
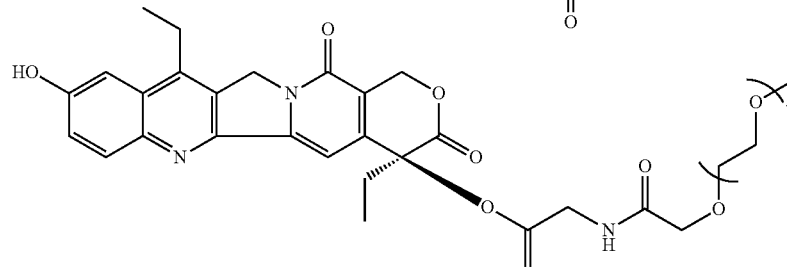
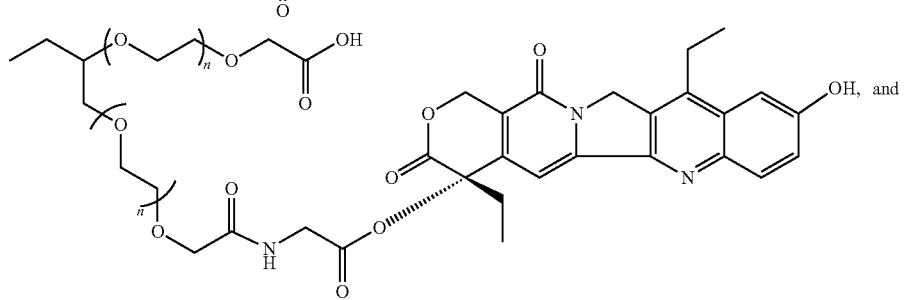

-continued
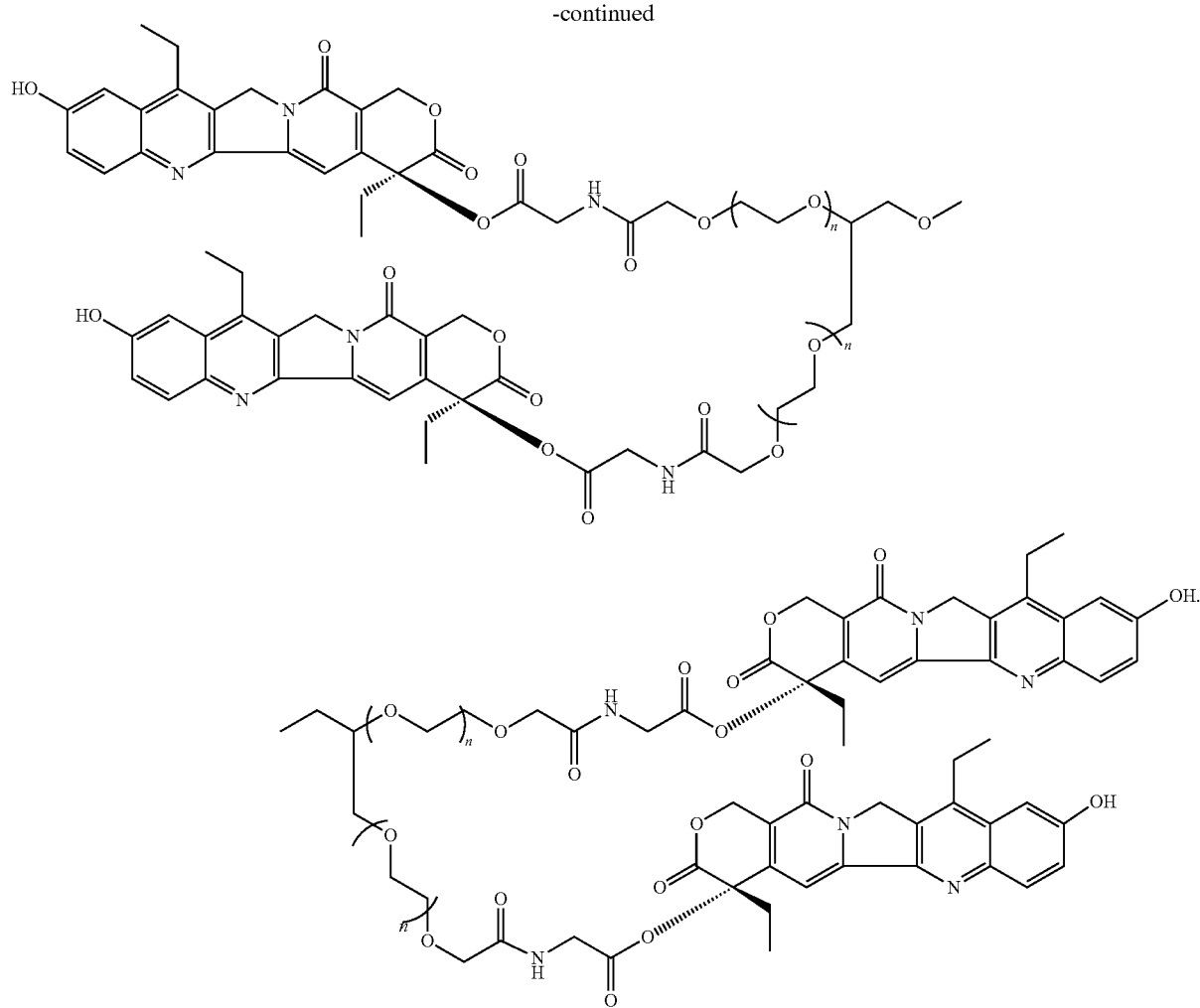
18. The method of claim 1, wherein the compound of formula (I) is
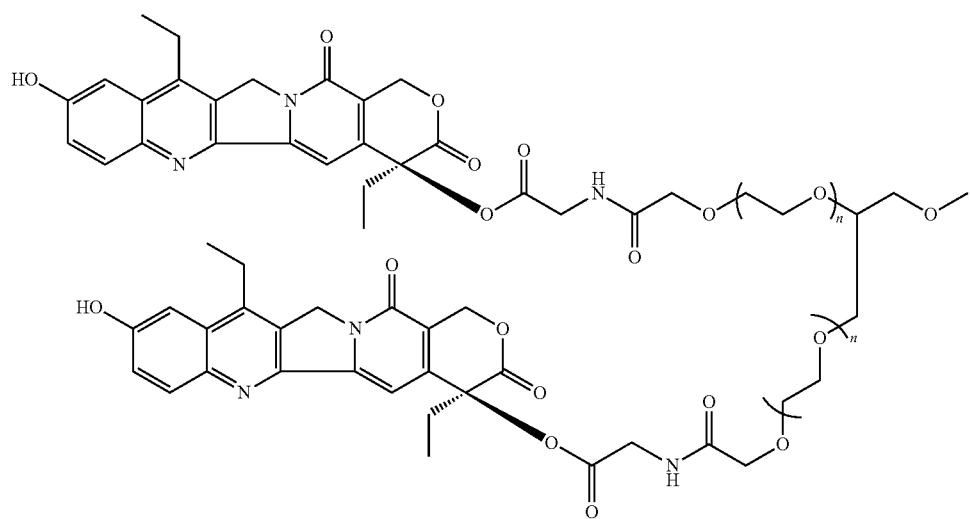

-continued

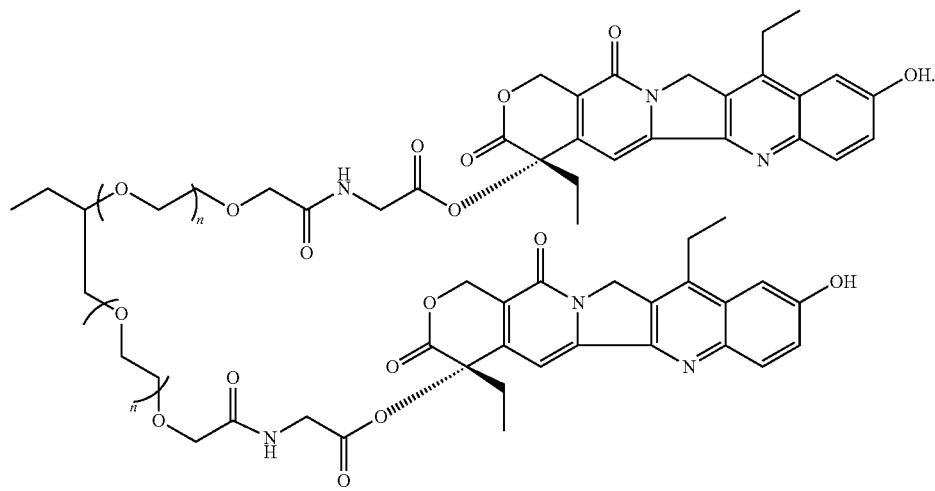

19. The method of claim 1, wherein the compound is administered in amounts of from about 0.1 to about 45 mg/m$^2$/dose, wherein the amount is the weight of 7-ethyl-10-hydroxycamptothecin included in the compound of formula (I).

20. The method of claim 1, wherein the compound is administered in amounts of from about 1.25 to about 16.5 mg/m$^2$/dose, wherein the amount is the weight of 7-ethyl-10-hydroxycamptothecin included in the compound of formula (I).

21. The method of claim 1, wherein the compound is administered in combination with a second chemotherapeutic agent simultaneously or sequentially.

22. A method of treating a resistant or refractory colorectal cancer in a mammal, comprising:

administering to said mammal having a resistant or refractory colorectal cancer an effective amount of a compound of

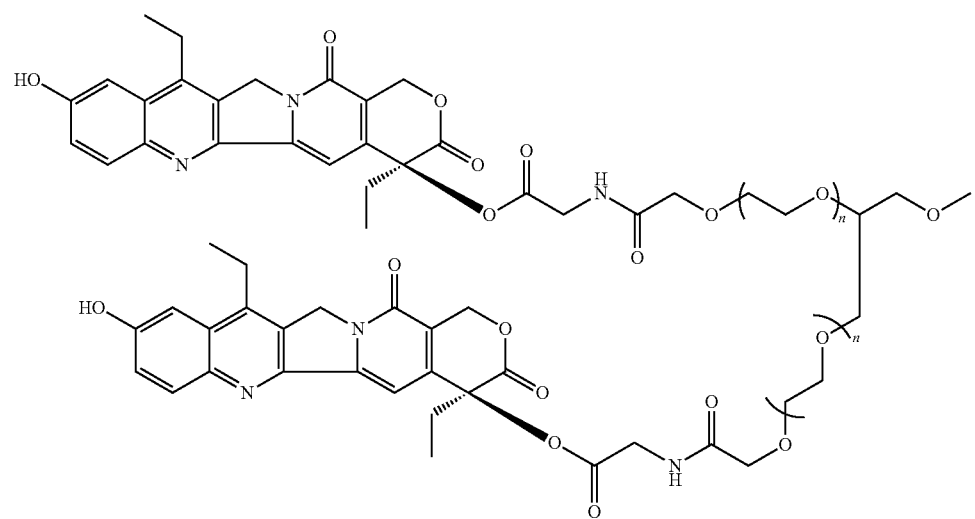

-continued

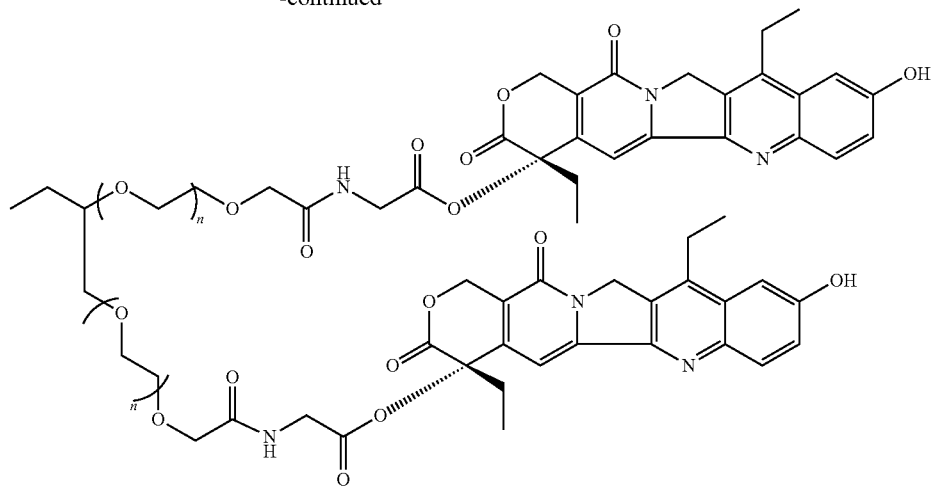

in amounts from about 1.25 to about 16.5 mg/m²/dose, wherein n is from about 28 to about 341 so that the total molecular weight of the polymeric portion of the compound ranges from about 5,000 to about 60,000 daltons; and the amount is the weight of 7-ethyl-10-hydroxycamptothecin included in the compound.

23. The method of claim 22, wherein the resistant or refractory colorectal cancer is resistant or refractory to camptothecin or CPT-11 and n is about 227 so that the total molecular weight of the polymeric portion of the compound is about 40,000 daltons.

24. The method of claim 23, wherein the resistant or refractory colorectal cancer is resistant or refractory to CPT-11 therapy.

25. The method of claim 23, wherein the resistant or refractory colorectal cancer expresses HIF-1α.

26. The method of claim 1, wherein the compound of formula (I) is administered in amounts of from about 0.1 mg/kg/dose to about 10 mg/kg/dose, and wherein the amount is the weight of 7-ethyl-10-hydroxycamptothecin included in the compound of formula (I).

27. The method of claim 22, wherein the compound is administered in amounts of from about 0.2 mg/kg/dose to about 10 mg/kg/dose, and wherein the amount is the weight of 7-ethyl-10-hydroxycamptothecin included in the compound.

28. The method of claim 5, wherein the resistant or refractory colorectal cancer expresses HIF-1α.

29. The method of claim 1, wherein the compound is administered intravenously.

* * * * *